(12) United States Patent
Sestito et al.

(10) Patent No.: US 10,351,548 B2
(45) Date of Patent: Jul. 16, 2019

(54) 2-OXO-1,2-DIHYDROPYRIDINE-3-CARBOXAMIDE COMPOUNDS AND THEIR USE AS INHIBITORS OF PDK1

(71) Applicant: INTERNATIONAL SOCIETY FOR DRUG DEVELOPMENT S.R.L., Milan (IT)

(72) Inventors: Simona Sestito, Chiaravalle Centrale (IT); Simona Daniele, Pisa (IT); Claudia Martini, Pisa (IT); Simona Rapposelli, Capannori (IT); Guido Puricelli, Milan (IT)

(73) Assignee: International Society for Drug Development S.R.L., Milan (IT)

( * ) Notice: Subject to any disclaimer, the term of this patent is extended or adjusted under 35 U.S.C. 154(b) by 0 days.

(21) Appl. No.: 15/735,468

(22) PCT Filed: Jun. 10, 2016

(86) PCT No.: PCT/EP2016/063293
§ 371 (c)(1),
(2) Date: Dec. 11, 2017

(87) PCT Pub. No.: WO2016/198597
PCT Pub. Date: Dec. 15, 2016

(65) Prior Publication Data
US 2018/0155320 A1 Jun. 7, 2018

(30) Foreign Application Priority Data
Jun. 11, 2015 (IT) .................. 102015000022831

(51) Int. Cl.
*C07D 401/12* (2006.01)
*C07D 401/14* (2006.01)
*C07D 409/14* (2006.01)
*A61P 35/00* (2006.01)
*A61K 31/4439* (2006.01)

(52) U.S. Cl.
CPC ........ *C07D 401/12* (2013.01); *A61K 31/4439* (2013.01); *A61P 35/00* (2018.01); *C07D 401/14* (2013.01); *C07D 409/14* (2013.01)

(58) Field of Classification Search
CPC ... C07D 401/12; C07D 401/14; C07D 409/14
See application file for complete search history.

(56) References Cited

FOREIGN PATENT DOCUMENTS

| WO | 2008/005457 A2 | 1/2008 |
|---|---|---|
| WO | 2010/065384 A1 | 6/2010 |

OTHER PUBLICATIONS

Sestito et al., European Journal of Medicinal Chemistry, 118 (published online Apr. 20, 2016), pp. 47-63 and the Supporting Information, pp. 1-16 (Year: 2016).*
International Search Report and Written Opinion for corresponding Application No. PCT/EP2016/063293 (dated Aug. 10, 2016).
Nagashima et al., "Genetic and Pharmacological Inhibition of PDK1 in Cancer Cells: Characterization of a Selective Allosteric Kinase Inhibitor," J. Biol. Chem. 286(8):6433-6448 (2011).

* cited by examiner

*Primary Examiner* — Laura L Stockton
(74) *Attorney, Agent, or Firm* — Pepper Hamilton LLP

(57) ABSTRACT

The present invention concern a 2-oxo-1,2-dihydropyridine-3-carboxamide compound of Formula (I) and new 2-oxo-1,2-dihydropyridine-3-carboxamide compounds of Formula (II) in the treatment of pathologies which require an inhibitor of PDK1 enzyme such as diabetes, neurodegenerative diseases such as Alzheimer's and Prion Diseases, and tumors such as breast, and pancreatic cancers and glioblastoma, particularly glioblastoma.

21 Claims, 7 Drawing Sheets

A

2-OXO-1,2-DIHYDROPYRIDINE-3-CARBOXAMIDE COMPOUNDS AND THEIR USE AS INHIBITORS OF PDK1

This application is a national stage application under 35 U.S.C. § 371 of PCT Application No. PCT/EP2016/063293, filed 10 Jun. 2016, which claims priority of Italy Application No. 102015000022831, filed 11 Jun. 2015.

FIELD OF INVENTION

The invention concerns 2-oxo-1,2-dihydropyridine-3-carboxamide compounds and their use as inhibitors and/or modulators of PDK1.

STATE OF THE ART

The PI3K/PDK1/Akt signaling axis is centrally involved in inhibition of apoptosis and stimulation of cell proliferation and it has been estimated that at least 50% of all cancer types are related to deregulation of this signaling pathway.

Due to its key function as regulator of cell survival and metabolism, the dysregulation of this pathway is manifested in several human pathologies including cancers and neurodegenerative diseases.

Phosphoinositide-dependent kinase (PDK1) acts as one of the main mediators of the pathway. PDK1 is a serine/threonine protein kinase that plays a key role in regulating cell growth, proliferation, and survival through both Akt-dependent and Akt-independent mechanisms. The Akt-dependent pathway is characterized by the implication of downstream proteins like mTOR, Ras and GSK, all controlled by Akt. The Akt-independent signal acts via PLCγ1, a phospholipase implicated in metastasis.

The phosphorylation and, therefore, activation of multiple substrates that seem to be constitutively active in tumor tissue (such as AKT, S6K, SGK, RSK and PKC isoforms) may explain the influence of this kinase on a variety of cellular processes including proliferation, migration and survival.

For these reasons, PDK1 also known as "master kinase" of the AGC kinases has attracted considerable interest as an anticancer drug target. However, although there have been done huge efforts in discovering specific molecules targeting PI3K and Akt, PDK1 has been rather overlooked. Recently the increasing interest in this kinase prompted many research groups to work in this direction, thus publishing and patenting several series of molecules able to inhibit this important node of the PI3K/PDK1/Akt.

PDK1 plays a pleiotropic role in growth and development. Recent findings revealed that elevated activation of PDK1 induces tumorigenesis by enhancing cell proliferation and inhibiting apoptosis. In addition, increasing evidence show that PDK1 plays a pivotal role in cell migration and metastasis. Its role in these processes was proved in different cell types and organisms including endothelial cells, smooth muscle cells, T lymphocytes, neutrophils and several tumour cell lines such as breast, glioblastoma (Signore, M., et al., Combined PDK1 and CHK1 inhibition is required to kill glioblastoma stem-like cells in vitro and in vivo. Cell death & disease, 2014. 5(5): p. e1223) and pancreatic cancers.

In WO2008/005457 new pyridinonyl compounds are described having PDK1 inhibition activity as demonstrated for some prepared compounds in vitro. The same compounds were also studied on cellular lines and the results are reported in Nagashima, K., et al., Genetic and Pharmacological Inhibition of PDK1 in Cancer Cells CHARACTERIZATION OF A SELECTIVE ALLOSTERIC KINASE INHIBITOR. Journal of Biological Chemistry, 2011. 286(8): p. 6433-6448. Even if some compounds were claimed as PDK1 inhibitors in WO2008/005457, they do not significantly inhibit cell growth on standard tissue cell culture, specifically on PC3 prostate cancer lines.

There is a great need for efficacious inhibitors against PDK1 enzyme.

SUMMARY OF THE INVENTION

The above object has been achieved by a 2-oxo-1,2-dihydropyridine-3-carboxamide compound of Formula (I)

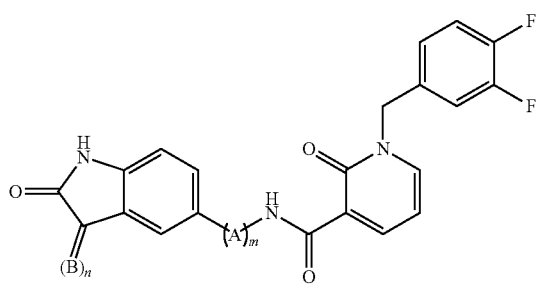

wherein
m is 0 or 1
n is 0 or 1
B is CH-D, where D is selected from the group consisting of thienyl, phenyl, imidazolyl, being D optionally substituted with a halogen; and
A is selected from the group consisting of (—NH—CO—CH$_2$—), (—NH—CO—CH(Ph)-), (—NH—CO—CH$_2$—CH$_2$—), (—NH—CO—CH$_2$—CH$_2$—CH$_2$—) and (—NH—CO-Ph),
or a pharmaceutical salt thereof for use in the treatment of pathologies requiring the use of an inhibitor of PDK1 enzyme.

In another aspect the invention concerns a new 2-oxo-1,2-dihydropyridine-3-carboxamide compound of Formula (II)

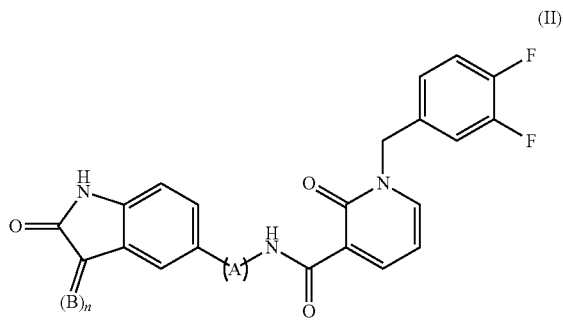

wherein
n is 0 or 1
B is CH-D, where D is selected from the group consisting of thienyl, phenyl, imidazolyl, being D optionally substituted with a halogen; and
A is selected from the group consisting of (—NH—CO—CH$_2$—), (—NH—CO—CH(Ph)-) (—NH—CO—CH$_2$—CH$_2$—) (—NH—CO—CH$_2$—CH$_2$—CH$_2$—) and (—NH—CO-Ph-),
or a pharmaceutical salt thereof.

In another aspect the invention concerns a compound of Formula (II) for use as a medicament.

In a further aspect the invention concerns a pharmaceutical composition comprising a compound of Formula (II) and a pharmaceutically acceptable carrier.

In a still further aspect the invention concerns a compound of Formula (II) for use in the treatment of pathologies requiring the use of a PDK1-inhibitor.

The pathologies that require a PDK1 enzyme inhibitor are diabetes, neurodegenerative diseases such as Alzheimer's and Prion Diseases, and tumours such as breast, and pancreatic cancers and glioblastoma. Preferably such pathology is a cancer, more preferably glioblastoma (GBM).

In this invention a compound of Formula (I) or Formula (II) may exist as R and S enantiomers and as racemic mixture. This invention includes in its scope of protection all the possible isomers and racemic mixtures. Wherever should be present further symmetry centers, this invention includes all the possible diastereoisomers and relative mixtures as well.

DETAILED DESCRIPTION OF THE INVENTION

Figure 1:
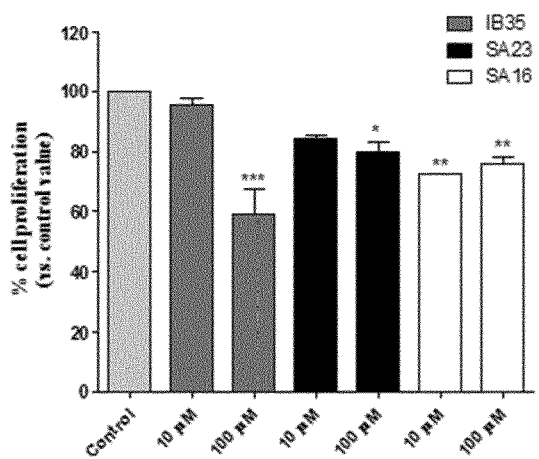
FIG. 1 illustrates the inhibition of U87MG cell proliferation after 24 h of incubation with compounds of the invention.

The invention hence concerns a 2-oxo-1,2-dihydropyridine-3-carboxamide compound of Formula (I)

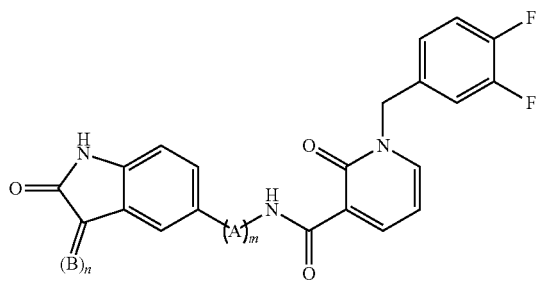

wherein
m is 0 or 1
n is 0 or 1
A is selected from the group consisting of (—NH—CO—CH$_2$—), (—NH—CO—CH(Ph)-), (—NH—CO—CH$_2$—CH$_2$—), (—NH—CO—CH$_2$—CH$_2$—CH$_2$—) and (—NH—CO-Ph-); and
B is CH-D, where D is selected from the group consisting of thienyl, phenyl, imidazolyl, being D optionally substituted with a halogen,
or a pharmaceutical salt thereof for use in the treatment of pathologies requiring the use of an inhibitor of PDK1 enzyme.

When m is 0, n is preferably 1.
When m is 1, n can be 0 or 1.
Preferably m is 1 and n is 1.
When m is 1 A is selected from the group consisting of (—NH—CO—CH$_2$—), (—NH—CO—CH(Ph)-), (—NH—CO—CH$_2$—CH$_2$—), (—NH—CO—CH$_2$—CH$_2$—CH$_2$—) and (—NH—CO-Ph-).

Preferably A is (—NH—CO—CH$_2$—), (—NH—CO—CH$_2$—CH$_2$—), (—NH—CO—CH$_2$—CH$_2$—CH$_2$—) or (—NH—CO-Ph-).

When n is 1, B is CH-D, where D is selected from the group consisting of thienyl, phenyl, imidazolyl, being D optionally substituted with a halogen.

Preferably D is imidazolyl, preferably 1H-imidazol-5-yl or 1H-imidazol-2-yl.

In a preferred embodiment A is (—NH—CO—CH(Ph)-) and D is imidazolyl, preferably 1H-imidazol-5-yl.

In a more preferred embodiment A is (—NH—CO—CH$_2$—) and D is imidazolyl, preferably 1H-imidazol-5-yl.

In a more preferred embodiment A is (—NH—CO—CH$_2$—CH$_2$) and D is imidazolyl, preferably 1H-imidazol-5-yl.

In a more preferred embodiment A is (—NH—CO—CH$_2$—CH$_2$) and D is imidazolyl, preferably 1H-imidazol-2-yl.

In a further preferred embodiment A is (—NH—CO—CH$_2$—CH$_2$—CH$_2$—) or (—NH—CO-Ph), more preferably D is imidazolyl, still more preferably 1H-imidazol-5-yl.

The preferred compound for the use as PDK1 inhibitor is one of the compounds reported in the Table below.

| Structure | IUPAC name |
|---|---|
| | JJ31<br>(Z)-N-(3-((1H-imidazol-5-yl)methylene)-2-oxoindolin-5-yl)-1-(3,4-difluorobenzyl)-2-oxo-1,2-dihydropyridine-3-carboxamide |
| | IB32<br>1-(3,4-difluorobenzyl)-2-oxo-N-(2-oxo-2-((2-oxoindolin-5-yl)amino)ethyl)-1,2-dihydropyridine-3-carboxamide |
| | IB36<br>(E/Z)-1-(3,4-difluorobenzyl)-2-oxo-N-(2-oxo-2-((2-oxo-3-(thiophen-2-ylmethylene)indolin-5-yl)amino)ethyl)-1,2-dihydropyridine-3-carboxamide |
| | IB35<br>(Z)-N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide |

-continued

| Structure | IUPAC name |
|---|---|
| 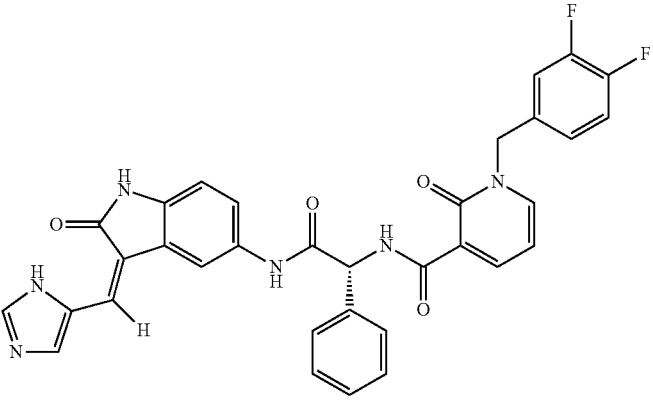 | SA16<br>(Z)-(R)-N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide |
| 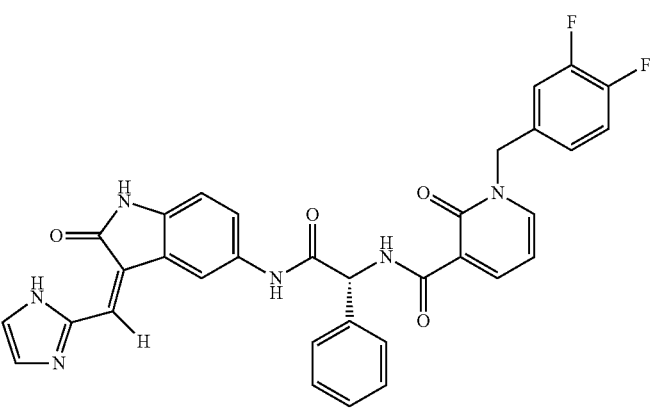 [SMILES: O=C1Nc2ccc(NC(=O)[C@H](NC(=O)c3cccn(Cc4ccc(F)c(F)c4)c3=O)c3ccccc3)cc2/C1=C/c1ncc[nH]1] | SA23<br>(Z)-(R)-N-(2-((3-((1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide |
| 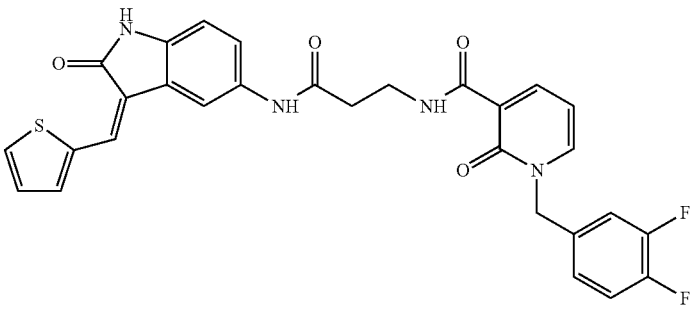 [SMILES: O=C(CCNC(=O)c1cccn(Cc2ccc(F)c(F)c2)c1=O)Nc1ccc2c(c1)/C(=C/c1cccs1)C(=O)N2] | DD22<br>(E/Z)-1-(3,4-difluorobenzyl)-2-oxo-N-(3-oxo-3-((2-oxo-3-(thiophen-2-ylmethylene)indolin-5-yl)amino)propyl)-1,2-dihydropyridine-3-carboxamide |
| 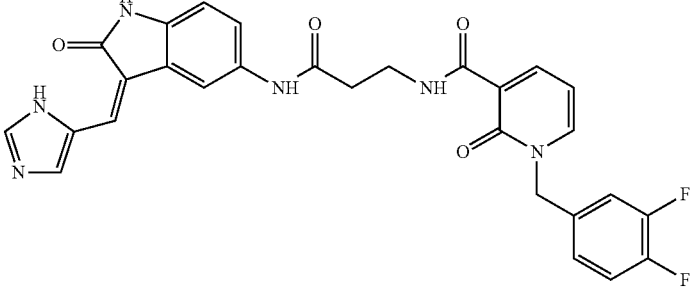 | DD21<br>(Z)-N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide |

-continued

| Structure | IUPAC name |
|---|---|
| | DD23<br>(E/Z)-1-(3,4-difluorobenzyl)-N-(3-((3-(4-fluorobenzylidene)-2-oxoindolin-5-yl)amino)-3-oxopropyl)-2-oxo-1,2-dihydropyridine-3-carboxamide |
| | DD25<br>(Z/E)-N-(3-((3-((1H-imidazol-2-yl)methylene)-2-oxoindolin-5-yl)amino)-3-oxopropyl)-1-(3,4-difluorobenzyl)-2-oxo-1,2-dihydropyridine-3-carboxamide |
| | DD40<br>(Z)-N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide |
| | DD41<br>(E/Z)-1-(3,4-difluorobenzyl)-2-oxo-N-(3-((2-oxo-3-(thiophen-2-ylmethylene)indolin-5-yl)carbamoyl)phenyl)-1,2-dihydropyridine-3-carboxamide |
| | DF8<br>(Z)-N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide |

-continued

| Structure | IUPAC name |
|---|---|
| 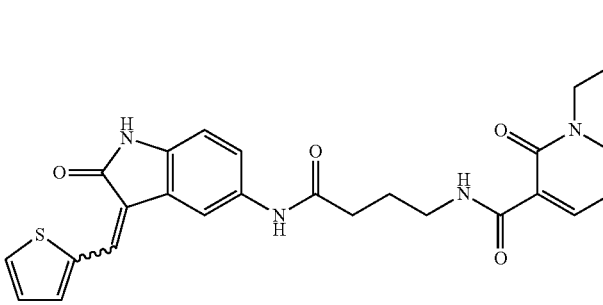 | DF9<br>(E/Z)-1-(3,4-difluorobenzyl)-2-oxo-N-(4-oxo-4-((2-oxo-3-(thiophen-2-ylmethylene)indolin-5-yl)amino)butyl)-1,2-dihydropyridine-3-carboxamide |

More preferably the compound of Formula (I) is selected from the group (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—(R)—N-(2-((3-((1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide and (Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide.

Still more preferably, the compound of Formula (I) is (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide.

Preferred compounds are also (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide and (Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide.

In another aspect the invention relates a 2-oxo-1,2-dihydropyridine-3-carboxamide compound of Formula (II)

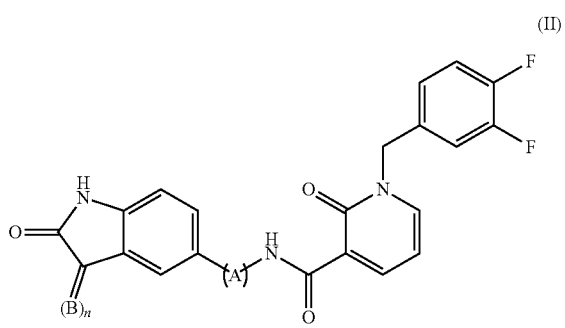

wherein n is 0 or 1

B is CH-D, where D is selected from the group consisting of thienyl, phenyl, imidazolyl, being D optionally substituted with a halogen; and A is selected from the group consisting of (—NH—CO—CH$_2$—), (—NH—CO—CH(Ph)-) (—NH—CO—CH$_2$—CH$_2$—), (—NH—CO—CH$_2$—CH$_2$—CH$_2$—) and (—NH—CO-Ph-), or a pharmaceutical salt thereof.

n is 0 or 1, more preferably n is 1.

A is selected from the group consisting of (—NH—CO—CH$_2$—), (—NH—CO—CH(Ph)-) (—NH—CO—CH$_2$—CH$_2$—), (—NH—CO—CH$_2$—CH$_2$—CH$_2$—) and (—NH—CO-Ph-). Preferably A is (—NH—CO—CH$_2$—), (—NH—CO—CH$_2$—CH$_2$—CH$_2$—), (—NH—CO—CH$_2$—CH$_2$—) or (—NH—CO-Ph-).

In a more preferred embodiment n is 1 and A is selected from the group consisting of (—NH—CO—CH$_2$—), (—NH—CO—CH$_2$—CH$_2$—) (—NH—CO—CH$_2$—CH$_2$—CH$_2$—) and (—NH—CO-Ph-).

When n is 1, B is CH-D, where D is selected from the group consisting of thienyl, phenyl, imidazolyl, being D optionally substituted with a halogen.

Preferably D is imidazolyl.

In a preferred embodiment A is (—NH—CO—CH(Ph)-) and D is imidazolyl, preferably 1H-imidazol-5-yl.

In a more preferred embodiment A is (—NH—CO—CH$_2$—) and D is imidazolyl, preferably 1H-imidazol-5-yl.

In a more preferred embodiment A is (—NH—CO—CH$_2$—CH$_2$—) and D is imidazolyl, preferably 1H-imidazol-5-yl.

The preferred compound is one of the compounds reported in the Table below.

| Structure | IUPAC name |
|---|---|
| 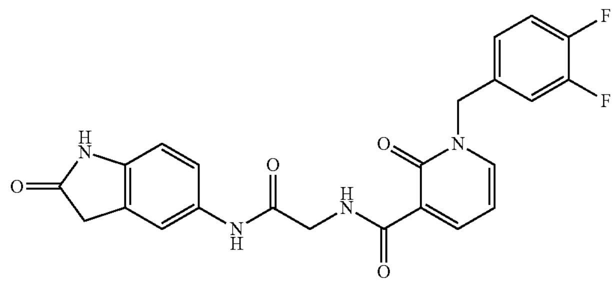 [SMILES: O=C(CNC(=O)c1cccn(Cc2ccc(F)c(F)c2)c1=O)Nc1ccc2c(c1)CC(=O)N2] | IB32<br>1-(3,4-difluorobenzyl)-2-oxo-N-(2-oxo-2-((2-oxoindolin-5-yl)amino)ethyl)-1,2-dihydropyridine-3-carboxamide |
| | IB36<br>(E/Z)-1-(3,4-difluorobenzyl)-2-oxo-N-(2-oxo-2-((2-oxo-3-(thiophen-2-ylmethylene)indolin-5-yl)amino)ethyl)-1,2-dihydropyridine-3-carboxamide |
| 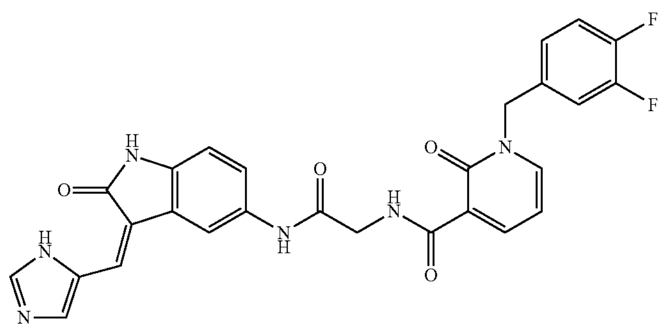 [SMILES: O=C(CNC(=O)c1cccn(Cc2ccc(F)c(F)c2)c1=O)Nc1ccc2c(c1)/C(=C/c1cnc[nH]1)C(=O)N2] | IB35<br>(Z)-N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide |
| 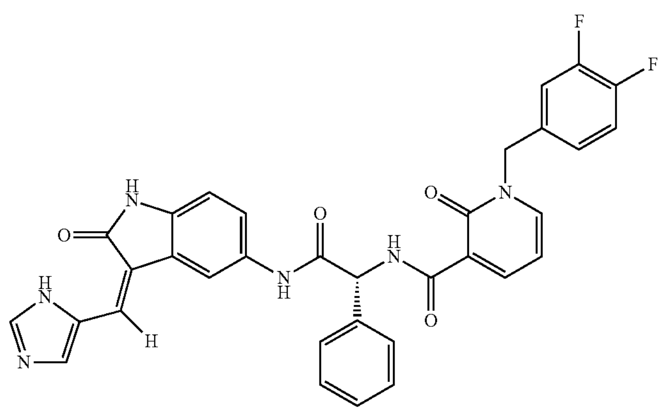 [SMILES: O=C1Nc2ccc(NC(=O)[C@H](NC(=O)c3cccn(Cc4ccc(F)c(F)c4)c3=O)c3ccccc3)cc2/C1=C/c1cnc[nH]1] | SA16<br>(Z)-(R)-N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide |

| Structure | IUPAC name |
|---|---|
| | SA23<br>(Z)-(R)-N-(2-((3-((1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide |
| | DD22<br>(E/Z)-1-(3,4-difluorobenzyl)-2-oxo-N-(3-oxo-3-((2-oxo-3-(thiophen-2-ylmethylene)indolin-5-yl)amino)propyl)-1,2-dihydropyridine-3-carboxamide |
| | DD21<br>(Z)-N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide |
| | DD23<br>(E/Z)-1-(3,4-difluorobenzyl)-N-(3-((3-(4-fluorobenzylidene)-2-oxoindolin-5-yl)amino)-3-oxopropyl)-2-oxo-1,2-dihydropyridine-3-carboxamide |

-continued

| Structure | IUPAC name |
|---|---|
| 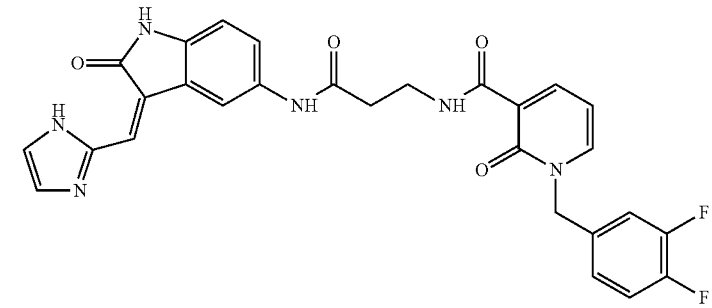 [SMILES: O=C(CCNC(=O)c1cccn(Cc2ccc(F)c(F)c2)c1=O)Nc1ccc2c(c1)/C(=C/c1cnc[nH]1)C(=O)N2] | DD25 (Z/E)-N-(3-((3-((1H-imidazol-2-yl)methylene)-2-oxoindolin-5-yl)amino)-3-oxopropyl)-1-(3,4-difluorobenzyl)-2-oxo-1,2-dihydropyridine-3-carboxamide |
| 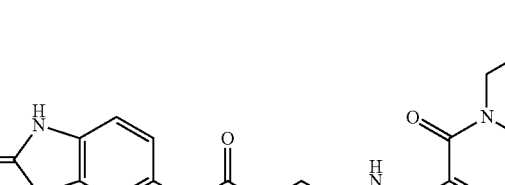 | DD40 (Z)-N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide |
| 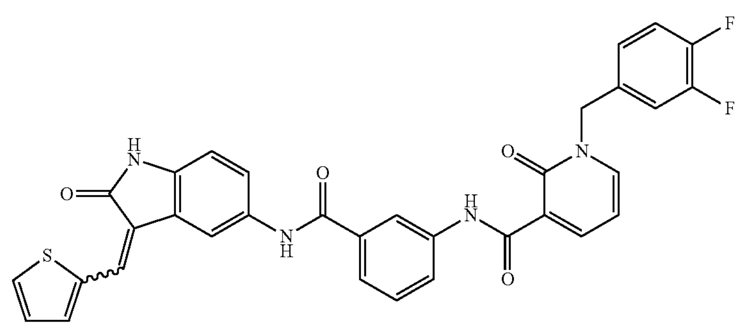 [SMILES: O=C1Nc2ccc(NC(=O)c3cccc(NC(=O)c4cccn(Cc5ccc(F)c(F)c5)c4=O)c3)cc2C1=Cc1cccs1] | DD41 (E/Z)-1-(3,4-difluorobenzyl)-2-oxo-N-(3-((2-oxo-3-(thiophen-2-ylmethylene)indolin-5-yl)carbamoyl)phenyl)-1,2-dihydropyridine-3-carboxamide |
| 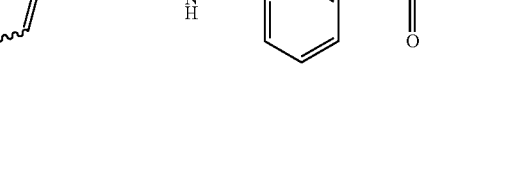 | DF8 (Z)-N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide |

| Structure | IUPAC name |
|---|---|
| 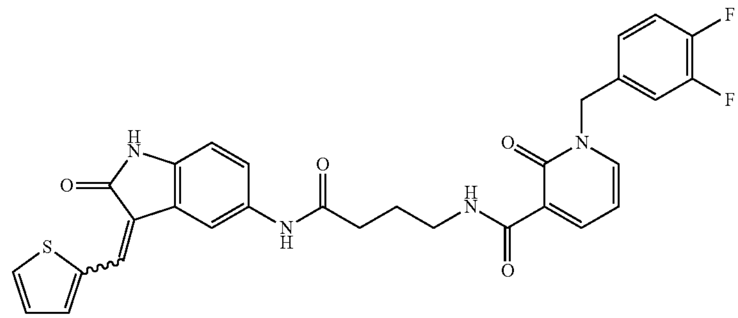 [SMILES: O=C(CCCNC(=O)c1cccn(Cc2ccc(F)c(F)c2)c1=O)Nc1ccc2c(c1)C(=Cc1cccs1)C(=O)N2] | DF9 (E/Z)-1-(3,4-difluorobenzyl)-2-oxo-N-(4-oxo-4-((2-oxo-3-(thiophen-2-ylmethylene)indolin-5-yl)amino)butyl)-1,2-dihydropyridine-3-carboxamide |

More preferably the compound of Formula (II) is selected from the group (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—(R)—N-(2-((3-((1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide and (Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide.

Still more preferably, the compound of Formula (II) is (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide.

Preferred compounds are also (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, or (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide or (Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide. The compounds of the invention can be prepared by using processes, easy to scale-up and avoiding lengthy and expensive preparation steps thus obtaining high yield of a stable pharmaceutical grade compound as it will be evident from the experimental part of the present description.

The compounds of the invention of Formulas (I) and (II) as such or a pharmaceutical salt thereof could be used in medicine in particular as inhibitor of PDK1 enzyme.

In another aspect, the present invention provides a pharmaceutical composition comprising a compound of Formula (I) and/or Formula (II) and a pharmaceutically acceptable excipient, for example a carrier. The pharmaceutical composition can also comprise a known PDK1 inhibitor compound.

The compounds of the invention of Formula (I) and of Formula (II) can be administered alone or can be coadministered to the patient. Coadministration is meant to include simultaneous or sequential administration of the compounds individually or in combination (more than one compound). Thus, the preparation can also be combined, when desired, with other active substances.

They could be used in combination with a pharmaceutically acceptable carrier and optionally with suitable excipients to obtain pharmaceutical compositions.

The term "pharmaceutically acceptable carrier" means solvents, carrier agents, diluting agents, and the like which are used in the administration of compounds of the invention.

Such pharmaceutical compositions can be administered by parenteral, oral, buccal, sublingual, nasal, rectal, topical or transdermal administration.

Compositions of the invention suitable for the oral administration will be conveniently discrete units such as tablets, capsules, cachet, powders or pellets or as liquid suspension.

The tablet can contain also suitable excipients routinely used in pharmaceutical field such as pre-gelatinized starch, microcrystalline cellulose, sodium glycolate starch, talc, lactose, magnesium stearate, sucrose, stearic acid, mannitol.

Compositions for parental administration may conveniently include sterile preparations.

Composition for topical administration may conveniently be formulated as creams, pastes, oils, ointments, emulsions, foams, gels, drops, spray solutions and transdermal patches.

The compounds of the invention can be used as a medicament in the treatment of pathologies which require an inhibitor of PDK1 enzyme such as cancers, preferably in the treatment of glioblastoma (GBM).

The compounds of Formula (I) and Formula (II) showed to inhibit the PDK1 enzyme with IC50 values in the range of nM to μM as it will be evident from the experimental part of the description.

The ranking of IC50 value on recombinant PDK1 reflected the affinity ranking towards glioblastoma cell lines, thus confirming that the antiproliferative activity is mediated by PDK1.

Advantageously the preferred compounds (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—(R)—N-(2-((3-((1H-imidazol-2-yl)methylene)-2-oxoindolin-2-yl)amino)-2-oxo-1-phenylethyl)-1-(3,4-difluorobenzyl)-2-oxo-1,2-dihydropyridine-3-carboxamide, (Z)—N-(3-((3-((1H-imidazol-5-yl)methylene)-2-oxoindolin-5-yl)carbamoyl)

phenyl)-1-(3,4-difluorobenzyl)-2-oxo-1,2-dihydropyridine-3-carboxamide, (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide and (Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide inhibited PDK1 constitutive activity in glioblastoma cells; as a result, the compounds of Formula (II) decreased cell viability, and triggered apoptosis. Moreover, the inhibition of cell viability was long-lasting. In the wound scratch assay as it will be clear below, PDK1 inhibitors showed to significantly inhibit cell migration, both after 6 h and 24 h from the scratch. These results confirmed that a PDK1 inhibition leads to a suppression of tumour cell migration.

Finally, the compounds of Formulas (I), and preferably of Formula (II), still more preferably the preferred compounds (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydro pyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—(R)—N-(2-((3-((1H-imidazol-5-yl)methylene)-2-oxoindolin-2-yl)amino)-2-oxo-1-phenylethyl)-1-(3,4-difluorobenzyl)-2-oxo-1,2-dihydropyridine-3-carboxamide (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, and (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide were characterized in glioma stem cells (GSCs) isolated from glioblastoma cells. The obtained results indicated that compounds induced a time- and concentration-dependent inhibition of GSC proliferation and triggered apoptosis, thus confirming that PDK1 inhibitors are capable to block GSC proliferation.

The invention will be now detailed by means of the following examples relating to the preparation of some invention compounds and to the evaluation of their activity against PDK1 receptor.

EXPERIMENTAL PARTS

Preparation of the Compounds of Formulas (I) and (II)

Commercial grade anhydrous solvents were used without further drying. Commercially available chemicals were purchased from Sigma-Aldrich or Alfa Aesar and used without further purification. Evaporation was performed in vacuum (rotating evaporator). Anhydrous $Na_2SO_4$ was always used as the drying agent.

Flash chromatography was performed on Merck 60 Å high-purity grade silica gel (0.40-63 μm). Reactions were followed by TLC, performed on Merck aluminium silica gel (60 F254) sheets. Spots were viewed under a UV lamp (254 nm) or with the aid 10% phosphomolybdic acid in EtOH. Melting points were determined with a Kofler hot-bench apparatus and were not corrected.

Hydrogenation reactions were performed through HG 2000 CLAIND® hydrogen generator. Microwave reaction were performed using CEM Discover® LabMate™ Microwave. Celite® 545 was used as filter agent.

$^1H$, $^{13}C$ and $^{19}F$ NMR spectra were obtained using a Bruker Avance 400 spectrometer and were recorder at 400, 101 and 376 MHz, respectively. $^1H$ NMR [t=373K] was recorded at 250 MHz on Bruker Avance II 250 spectrometer.

Chemical shifts are reported in parts per million (ppm) δ values, downfield from the internal reference tetramethylsilane (TMS) and referenced from solvent resonance as the internal standard: deuterochloroform [δ 7.26 ($^1H$ spectra), δ 77.16 ($^{13}C$ spectra)]; deuterodimethylsulfoxide [δ 2.50 ($^1H$ spectra), δ 39.52 ($^{13}C$ spectra)]; deuteroacetonitrile [δ 1.94 ($^1H$ spectra)]. Coupling constants J are reported in hertz (Hz). $^{19}F$ and $^{13}C$ NMR spectra are $^1H$ decoupled. $^{19}F$ NMR spectra are unreferenced, corrected from Trifluoroacetic Acid (TFA) as external standard (−76.2 ppm).

Signal patterns are indicated as follows: singlet (s), doublet (d), triplet (t), double-doublet (dd), double-triplet (dt), multiplet (m), broad singlet (br s), broad doublet (br d) and broad triplet (br t).

When the amide nitrogen bears two substituents, the $^1H$ NMR spectra show the presence of two different rotamers in equilibrium.

The elemental compositions of the compounds (C, H, N) agreed to within (±) 0.4% of the theoretical values. When the elemental analysis is not included, compounds were used in the next step without further purification.

Abbreviations: TBTU=N,N,N',N'-Tetramethyl-O-(benzotriazol-1-yl)uronium tetrafluoroborate; DIPEA=N,N-Diisopropylethylamine; DMF=N,N-Dimethylformamide; CDI=N,N'-carbonyldiimidazole; TFA=Trifluoroacetic acid; NaH=Sodium hydride; DCM=dichloromethane Example 1: Preparation of Compound JJ31

(Z)—N-(3-((1H-imidazol-5-yl)methylene)-2-oxoindolin-5-yl)-1-(3,4-difluorobenzyl)-2-oxo-1,2-dihydropyridine-3-carboxamide The compound JJ31 was prepared by following Scheme 1

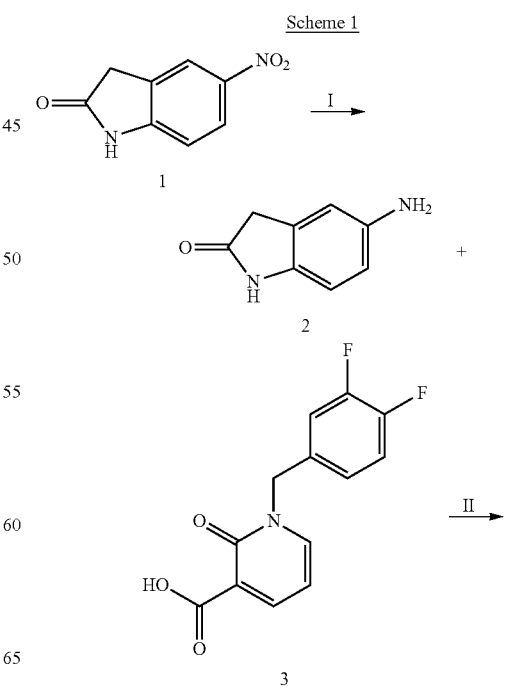

Scheme 1

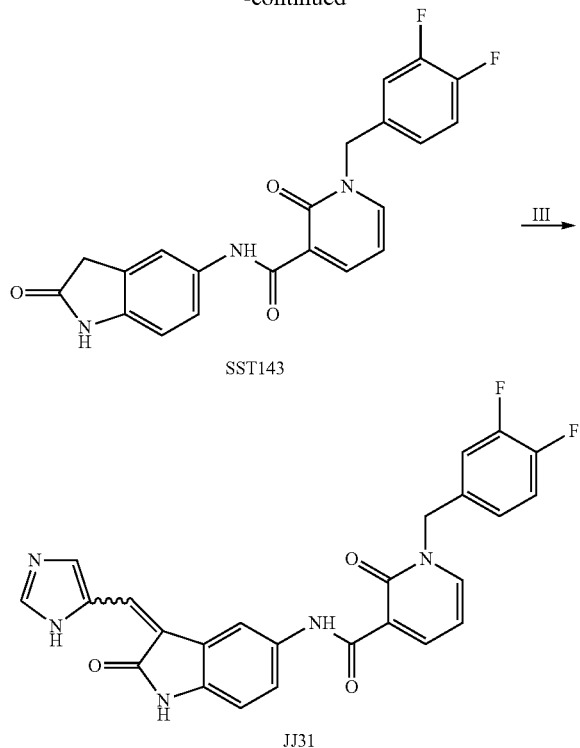

<sup>a</sup>Reagents and Conditions: I) H₂, Pd-C 10%, absolute EtOH, r.t., 4 h; II) TBTU, DIPEA, dry DMF, 0° C. → r.t., 12 h; III) 1H-imidazole-5-carbaldehyde, absolute EtOH, piperidine, 110° C., 4 h.

The catalytic hydrogenation of 5-nitro-oxindole in absolute EtOH in presence of Pd—C 10% gave the amine 2. The condensation of the carboxylic acid 3 with TBTU and DIPEA in dry DMF for 16 h, gave compound SST143. Compound 3 was synthesised through alkylation with 3,4-difluoro-benzylbromide of the 2-oxo-pyridine-3-carboxylic acid in presence of NaH 60%. The subsequent condensation of derivative SST143 with 1H-imidazole-5-carbaldehyde, and a catalytic amount of piperidine, gave the corresponding compound of the title. The 3-substituted 2-oxindole may exist as either the Z or E isomer depending on the characteristics of the substituents at the C3 position of the 2-oxindole nucleus. The configurations of the compounds were assigned by analyzing their $^1$H NMR spectra.

Synthesis of 5-amino-1,3-dihydro-2H-indol-2-one (2)

The 5-nitro-2-oxindole 1 (1.00 g, 5.61 mmol) was hydrogenated in EtOH (70 mL) in the presence of 10% Pd—C (315 mg, 2.97 mmol) for 4 h at room temperature. Then the catalyst was filtered off through Celite, the Celite rinsed with additional EtOH and the solution was evaporated, to give 2 as a brown solid (698 mg, 4.71 mmol, 84% yield).
$^1$H-NMR (400 MHz, DMSO-d₆): δ 3.30 (s, 2H, CH₂); 4.62 (br s, 2H, NH₂); 6.37 (dd, 1H, J=2.2, 8.2 Hz, Ar); 6.48-6.50 (m, 2H, Ar); 9.90 (br s, 1H, NH) ppm. Anal. Calcd for C₈H₈N₂O: C, 64.85%; H, 5.44%; N, 18.91%; Found: C, 65.03%; H, 5.49%; N, 18.83%.

Synthesis of 1-(3,4-difluorobenzyl)-2-oxo-1,2-dihydropyridine-3-carboxylic acid (3)

A stirred suspension of NaH 60% dispersion in mineral oil (206 mg, 5.14 mmol), washed twice with distilled n-hexane and once with Et₂O in 2 mL of anhydrous DMF under N₂ atmosphere was treated dropwise with a solution containing the 2-hydroxynicotinic acid (600 mg, 4.31 mmol) in 5 mL of anhydrous DMF. The mixture was left under stirring at room temperature for 2 h and then 3,4-difluoro-benzylbromide (1.06 g, 5.14 mmol) was added and the mixture stirred and heated at 50° C. for 16 h. After the mixture was concentrated under reduced pressure and the residue was treated with water to give a solid, which was collected by vacuum filtration. Next the solid was refluxed for 4 h in aq. 10% NaOH (10 mL) and the resulting mixture was cooled and made acid with 1N aq. HCl. The white solid formed was collected by filtration and washed with n-hexane and Et₂O, giving the derivative 3.9 as white solid (857 mg, 3.23 mmol, 75% yield).
$^1$H-NMR (400 MHz, DMSO-d₆): δ 5.30 (s, 2H, CH₂); 6.78 (t, 1H, J=6.9 Hz, Ar); 7.22-7.24 (m, 1H, Ar); 7.41-7.53 (m, 2H, Ar); 8.41 (d, 2H, J=6.9 Hz, Ar) ppm. Anal. Calcd for C₁₃H₉NO₃F₂: C, 58.87%; H, 3.42%; N, 5.28%; Found: C, 58.99%; H, 3.47%; N, 5.43%.

Synthesis of 1-(3,4-difluorobenzyl)-2-oxo-N-(2-oxoindolin-5-yl)-1,2-dihydropyridine-3-carboxamide (SST143)

The carboxylic derivative 3 (300 mg, 1.13 mmol) and the amine 2 (168 mg, 1.13 mmol) were combined through a condensation reaction in presence of the condensing agent TBTU (363 mg, 1.13 mmol). The solvents were evaporated under reduced pressure and the crude product was purified by flash chromatography over silica gel, using 0-4% MeOH as a gradient in CHCl₃, to obtain pure SST143 as a white solid (210 mg, 0.53 mmol, 47% yield).
mp: 285-288° C. $^1$H-NMR (400 MHz, DMSO-d₆): δ 3.48 (s, 2H, CH₂ indole); 5.28 (s, 2H, CH₂); 6.68 (dd, 1H, J=6.8, 7.2 Hz, Ar); 6.77 (d, 1H, J=8.4 Hz, Ar); 7.20-7.23 (m, 1H, Ar); 7.40-7.52 (m, 3H, Ar); 7.66 (s, 1H, Ar); 8.29 (dd, 1H, J=2.2, 6.8 Hz, Ar); 8.46 (dd, 1H, J=2.2, 6.8 Hz, Ar); 10.33 (s, 1H, NH), 11.87 (s, 1H, NH) ppm. $^{13}$C-NMR (101 MHz, DMSO-d₆): δ 176.23, 161.54, 160.73, 150.35, 147.90, 143.78, 143.42, 139.86, 134.02, 132.32, 126.40, 124.90, 120.35, 119.02, 117.74, 117.25, 116.90, 109.10, 107.22, 51.45, 36.02 ppm. $^{19}$F-NMR (376 MHz; DMSO-d₆): δ −138.17 (d, 1F, J=24 Hz); −139.76 (d, 1F, J=24 Hz) ppm. Anal. Calcd for C₂₁H₁₅F₂N₃O₃: C, 63.80%; H, 3.82%; N, 10.63%; Found: C, 63.72%; H, 3.55%; N, 10.50%.

Synthesis of (Z)—N-(3-((1H-imidazol-5-yl)methylene)-2-oxoindolin-5-yl)-1-(3,4-difluorobenzyl)-2-oxo-1,2-dihydropyridine-3-carboxamide (JJ31)

The crude product was purified by crystallization from EtOH, affording the Z-isomer as a yellow solid (29 mg, 0.06 mmol, 34% yield).
mp: 285-288° C. $^1$H-NMR (400 MHz, DMSO-d₆): δ 5.31 (s, 2H, CH₂); 6.70 (dd, 1H, J=6.8, 7.2 Hz, Ar); 6.87 (d, 1H, J=8.4 Hz, Ar); 7.22-7.25 (m, 1H, Ar); 7.42-7.62 (m, 3H, Ar); 7.68 (s, 1H, Ar); 7.94 (s, 1H, CH═); 8.01 (s, 1H, Ar); 8.03 (s, 1H, Ar); 8.32 (d, 1H, J=7.2 Hz, Ar); 8.50 (d, 1H, J=6.8 Hz, Ar); 11.00 (s, 1H, NH); 11.99 (s, 1H, NH) ppm. $^{13}$C-NMR (101 MHz, DMSO-d₆): δ 169.05, 161.58, 160.85, 150.36, 147.91, 143.85, 143.55, 139.67, 138.75, 136.10, 134.04, 132.79, 128.13, 124.85, 123.45, 120.29, 119.87, 117.86, 117.69, 117.25, 117.08, 111.39, 109.94, 107.28, 51.53 ppm. $^{19}$F-NMR (376 MHz; DMSO-d₆): −138.13 (d, 1F, J=24 Hz); −139.76 (d, 1F, J=24 Hz) ppm. Anal. Calcd for $C_{25}H_{17}F_2N_5O_3$: C, 63.15%; H, 4.03%; N, 14.73%; Found: C, 63.34%; H, 4.17%; N, 14.89%.

Example 2

Preparation of Compounds IB35, IB36, SA16, SA23, DD21-23, DD25, DF8 and DF9

The compounds IB35, IB36, SA16, SA23, DD21-23, DD25, DF8 and DF9 were prepared by following Scheme 2

Scheme 2

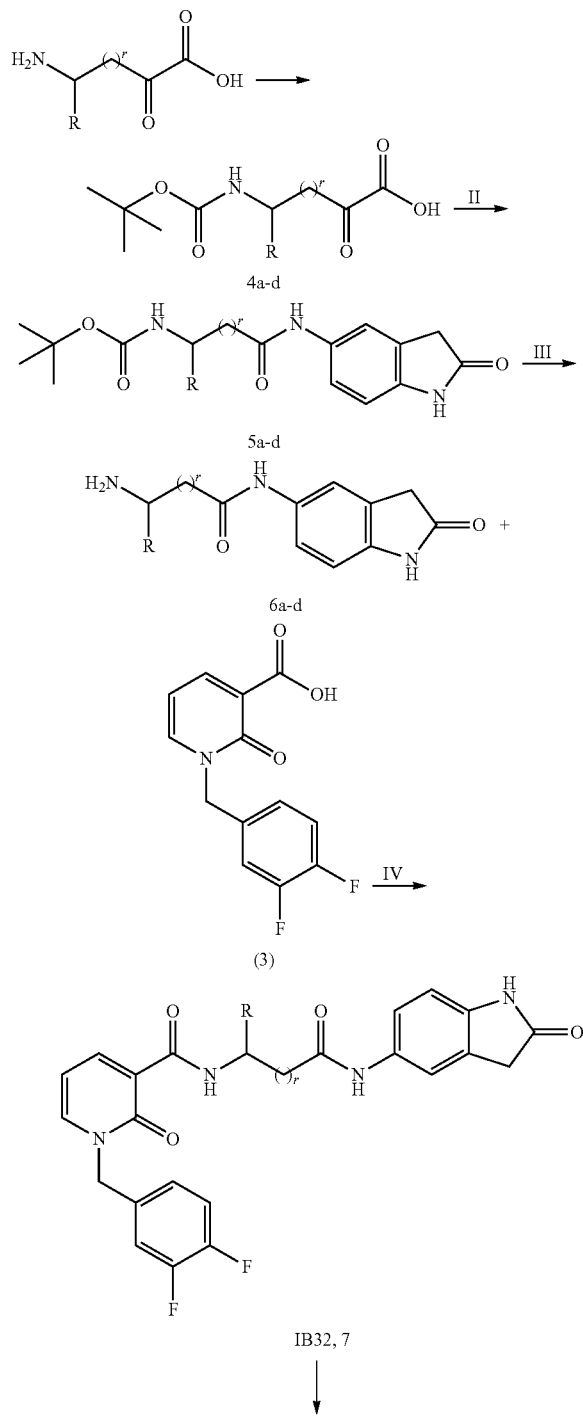

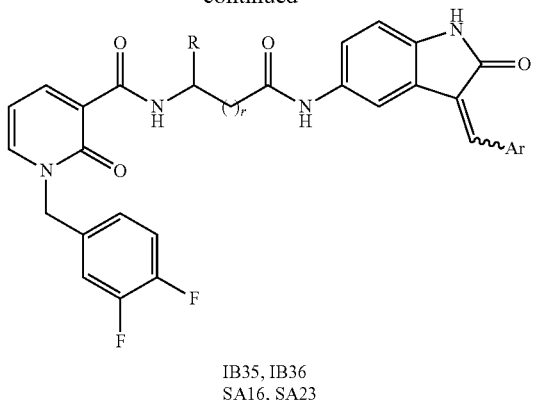

IB35, IB36
SA16, SA23
DD21-23,25
DF8, DF9

Reagents and conditions[a]: I) (Boc)$_2$O, NaOH 1 M/iPrOH 4:3, r.t., 2 h; II) 5-amino-2-oxo-indole, TBTU, DIPEA, dry DMF, r.t., 16 h; III) TFA, DCM, -10° C./-20° C., 3 h; IV) TBTU, DIPEA, dry DMF, r.t., 16 h; V) Appropriate carbaldehyde, iPrOH, DMF, piperidine, 110° C., 4 h (r = 0 and R = H IB32, IB35, IB36; r = 0 and R = Phenyl SA16 and SA23; r = 1 and R = H D21, D22, D23, DD25; r = 2 and R = H, DF8, DF9)

The compounds of Formula (II) were synthesised by the insertion of a linker to tether the 2-oxindole nucleus and the difluoro-benzylpyridonyl core. The synthetic procedure was carried out through amide condensation by using as spacer amino acids, such as glycine, (R)-(−)-2-phenylglycine or β-alanine.

The appropriate aminoacid was protected on amine group with (Boc)$_2$O and condensed with 5-amino-oxindole, leading to the amide derivative 5a-d.

Subsequently the deprotection reaction with trifluoroacetic acid afforded the amine 6a-d as trifluoroacetic salt, which was reacted with carboxylic acid 3 to give the derivative IB32 or 7. Knovenagel reaction with the appropriate carbaldehyde, in the presence of a catalytic amount of piperidine, provided the final desired compounds IB35-36, SA16, SA23, DD21-23, DD25, DF8 and DF9.

As previously observed the new compounds were obtained as Z E or E/Z mixture isomeric form. Again the configurations were assigned by analyzing their $^1$H NMR spectra.

General Procedure for the Synthesis of N-(Tert-Butoxycarbonyl)Aminoacid Derivatives (4a-d)

To a solution of appropriate aminoacid (13.32 mmol) in 1M NaOH/iPrOH (4:3) was added Boc$_2$O (2.9 g, 13.32 mmol). The reaction, monitored by TLC, was stirred at room temperature for 2 h and then washed with Et$_2$O, acidified to pH 3.0 with 1N HCl and finally extracted several time with AcOEt. The organic layer was dried over anhydrous Na$_2$SO$_4$ and evaporated under reduced pressure. The crude product 4a-d was used for the next step without further purification (1.68 g, 9.59 mmol, 72% yield).

2-((tert-butoxycarbonyl)amino)acetic acid (4a)

$^1$H-NMR (400 MHz, CDCl$_3$): δ 1.45 (s, 9H, Boc); 3.90-4.08 (m, 2H, CH$_2$); 5.07 (br s, 1H, NH) ppm. Anal. Calcd for $C_7H_{13}NO_4$: C, 47.99%; H, 7.48%; N, 8.00%; Found: C, 48.18%; H, 7.36%; N, 8.26%.

(R)-2-((tert-butoxycarbonyl)amino)-2-phenylacetic acid (4b)

$^1$H-NMR (400 MHz, CDCl$_3$): δ 1.21 (s, 6H, Boc); 1.43 (s, 3H, Boc); 5.12-5.51 (m, 1H); 7.29-7.44 (m, 5H); 7.96 (br s, 1H, NH) ppm. Anal. Calcd for C$_{13}$H$_{17}$NO$_4$: C, 62.14%; H, 6.82%; N, 5.57%; Found: C, 62.18%; H, 7.06%; N, 5.86%.

3-((tert-butoxycarbonyl)amino)propanoic acid (4c)

$^1$H-NMR (400 MHz, CDCl$_3$): δ 1.43 (br s, 9H, Boc); 2.52-2.59 (m, 2H); 3.39-3.41 (br s, 2H); 5.05-5.17 (m, 1H); Anal. Calcd for C$_8$H$_{15}$NO$_4$: C %, 50.78%; H, 7.99; N, 7.40; Found %: C, 51.02; H, 8.02; N, 7.54.

4-((tert-butoxycarbonyl)amino)butanoic acid (4d)

The crude product (921 mg, 4.53 mmol, 50% yield) was used for the next step without further purification. $^1$H NMR (400 MHz, CDCl$_3$): δ 1.44 (s, 9H, CH$_3$); 1.79-1.86 (m, 2H, CH$_2$); 2.40 (t, 2H, J=7.2 Hz, CH$_2$); 3.20-3.18 (m, 2H, CH$_2$) ppm. Anal. Calcd for C$_9$H$_{17}$NO$_4$: C, 53.19%; H, 8.43%; N, 6.89%; Found: C, 53.07%; H, 8.57%; N, 6.93%.

General Procedure for the Synthesis of Compounds 5a-d

N-Boc derivative 4a-d (2.64 mmol) was reacted through a condensation reaction with 5-amino-indol-2-one (391 mg, 2.64 mmol), in the presence of the condensing agent TBTU (848 mg, 2.64 mmol) and DIPEA (5.28 mmol, 0.92 mL) as a base.

tert-butyl (2-oxo-2-((2-oxoindolin-5-yl)amino)ethyl) carbamate (5a)

The amide was obtained after purification of the crude product by column chromatography over silica gel using CHCl$_3$/MeOH 92:8 as the eluent (693 mg, 2.27 mmol, 86% yield). $^1$H-NMR (400 MHz, DMSO-d$_6$): δ 1.39 (s, 9H, Boc); 3.46 (s, 2H, CH$_2$ indole); 3.68 (d, 2H, J=6.0 Hz, CH$_2$ glycine); 6.73 (d, 1H, J=8.2 Hz, Ar); 7.00 (t, 1H, J=6.0 Hz, NH); 7.32 (dd, 1H, J=2.0, 8.2 Hz, Ar); 7.49 (s, 1H, Ar); 9.74 (br s, 1H, NH); 10.27 (br s, 1H, NH) ppm. Anal. Calcd for C$_{16}$H$_{19}$N$_3$O$_4$: C, 59.01%; H, 6.27%; N, 13.76%; Found: C, 59.10%; H, 6.19%; N, 13.99%.

(R)-tert-butyl (2-oxo-2-((2-oxoindolin-5-yl)amino)-1-phenylethyl)-carbamate (5b)

Final compound has been purified by column chromatography over silica gel using CHCl$_3$/MeOH 92:8 as the eluent. $^1$H-NMR (400 MHz, DMSO-d$_6$): δ 1.39 (s, 9H, Boc); 3.44 (s, 2H, CH$_2$ indole); 5.30-5.33 (m, 1H); 6.72 (d, 1H, J=8.4 Hz, Ar); 7.26-7.36 (m, 4H, Ar); 7.44-7.48 (m, 4H, Ar); 10.09 (br s, 1H, NH); 10.29 (br s, 1H, NH) ppm. Anal. Calcd for C$_{21}$H$_{23}$N$_3$O$_4$: C, 66.13%; H, 6.08%; N, 11.02%; Found: C, 66.17%; H, 6.23%; N, 11.21%.

3-((tert-butoxycarbonyl)-amino)-N-(2-oxo-2,3-dihydro-1H-indol-5-yl)propanamide (5c)

Final compound has been purified by column chromatography over silica gel using CHCl$_3$/MeOH 92:8 as the eluent. $^1$H-NMR (400 MHz, DMSO-d$_6$): δ 1.39 (s, 9H, Boc); 2.42 (t, 2H, J=7.2 Hz); 3.16-3.22 (m, 2H); 3.45 (s, 2H); 6.71 (d, 1H, J=8.2 Hz, Ar); 6.84-6.88 (m, 1H); 7.32 (d, 1H, J=8.2 Hz); 7.50 (s, 1H, Ar); 9.78 (br s, 1H, NH); 10.28 (br s, 1H, NH) ppm. Anal. Calcd for C$_{16}$H$_{20}$N$_3$O$_4$: C, 60.37%; H, 6.33%; N, 13.20%; Found: C, 60.17%; H, 6.23%; N, 13.22%.

4-((tert-butoxycarbonyl)-amino)-N-(2-oxo-2,3-dihydro-1H-indol-5-yl)butanamide (5d)

Final compound (726 mg, 1.92 mmol, 95% yield) has been purified by column chromatography over silica gel using CHCl$_3$/MeOH (95:5) as the eluent. $^1$H NMR (400 MHz, DMSO-d$_6$): δ 1.37 (s, 9H, CH$_3$); 1.65-1.69 (m, 2H, CH$_2$); 2.24 (t, 2H, J=7.6 Hz, CH$_2$); 2.92-2.97 (m, 2H, CH$_2$); 3.44 (s, 2H, CH$_2$); 6.71 (d, 1H, J=8.2 Hz, Ar); 6.79 (br s, 1H, NH); 7.30 (d, 1H, J=8.2 Hz, Ar); 7.49 (s, 1H, Ar); 9.68 (br s, 1H, NH); 10.23 (br s, 1H, NH) ppm. Anal. Calcd for C$_{17}$H$_{23}$N$_3$O$_4$: C, 61.25%; H, 6.95%; N, 12.60%; Found: C, 60.98%; H, 6.89%; N, 12.41%.

General Procedure for the Synthesis of Compounds 6a-d

To a stirred suspension of 5a-d (2.27 mmol) in DCM (4.54 mL) cooled at −10° C./−20° C., was added TFA (4.54 mL). The reaction was monitored by TLC and reached completion in 3 h at the same temperature. Then the reaction mixture was evaporated to dryness to afford 6a-d as a trifluoroacetic salt, used for the following step without further purifications.

2-oxo-2-((2-oxoindolin-5-yl)amino)ethanaminium 2,2,2-trifluoro-acetate (6a)

$^1$H-NMR (400 MHz, DMSO-d$_6$): δ 3.49 (s, 2H, CH$_2$ indole); 3.74 (d, 2H, J=5.6 Hz, CH$_2$ glycine); 6.78 (d, 1H, J=8.0 Hz, Ar); 7.33 (dd, 1H, J=2.2, 8.2 Hz, Ar); 7.47 (s, 1H, Ar); 8.09 (br s, 3H, NH$_3^+$); 10.26 (br s, 1H, NH); 10.34 (br s, 1H, NH) ppm.

(R)-2-oxo-2-((2-oxoindolin-5-yl)amino)-1-phenylethanaminium 2,2,2-trifluoroacetate (6b)

$^1$H-NMR (400 MHz, DMSO-d$_6$): δ 3.47 (s, 2H, CH$_2$); 5.03-5.05 (m, 1H); 6.76 (d, 1H, J=8.4 Hz, Ar); 7.29 (dd, 1H, J=2.0, 8.4 Hz, Ar); 7.42-7.50 (m, 3H, Ar); 7.57-7.59 (m, 2H, Ar); 8.72-8.74 (m, 1H, Ar); 10.36 (br s, 1H, NH); 10.47 (br s, 1H, NH) ppm.

3-amino-N-(2-oxo-2,3-dihydro-1H-indol-5-yl)propanamide (6c)

$^1$H-NMR (400 MHz, DMSO-d$_6$): δ 2.66 (t, 2H, J=6.8 Hz); 3.06-3.11 (m, 2H); 3.49 (s, 2H, CH$_2$ indole); 6.75 (d, 1H, J=8.4 Hz, Ar); 7.33 (dd, 1H, J=2.0, 8.4 Hz, Ar); 7.50 (s, 1H, Ar); 7.79 (br s, 3H, NH$_3^+$); 10.02 (br s, 1H, NH); 10.33 (br s, 1H, NH) ppm.

4-amino-N-(2-oxo-2,3-dihydro-1H-indol-5-yl)butanamide (6d)

$^1$H NMR (400 MHz, DMSO-d$_6$): δ 1.82-1.85 (m, 2H, CH$_2$); 2.38 (t, 2H, J=6.8 Hz, CH$_2$); 2.83-2.85 (m, 2H, CH$_2$); 3.45 (s, 2H, CH$_2$); 6.73 (d, 1H, J=8.0 Hz, Ar); 7.31 (d, 1H, J=8.0 Hz, Ar), 7.50 (s, 1H, Ar); 7.76 (br s, 3H, NH$_3^+$); 9.84 (br s, 1H, NH); 10.29 (br s, 1H, NH) ppm.

1-(3,4-difluorobenzyl)-2-oxo-N-(4-oxo-4-((2-oxoindolin-5-yl)amino)butyl)-1,2-dihydropyridine-3-carboxamide. (7)

Carboxylic acid 3 (480 mg, 1.81 mmol) was reacted through a condensation reaction with the amine salt 6d (480 mg, 1.81 mmol), in the presence of TBTU (581.16 mg, 1.81 mmol). The procedure followed is the same described for derivative SST143 in example 1. The crude product was purified by flash chromatography over silica gel, using $CHCl_3$/MeOH (92:8) as the eluent, to obtain pure 7 as a white solid (680 mg, 1.42 mmol, 79% yield).

Mp: 199-204° C. $^1$H NMR (400 MHz, DMSO-$d_6$): δ 1.76-1.84 (m, 2H, $CH_2$); 2.30 (t, 2H, J=7.6 Hz, $CH_2$); 3.34-3.36 (m, 2H, $CH_2$); 3.43 (s, 2H, $CH_2$); 5.20 (s, 2H, $CH_2$); 6.57 (t, 1H, J=7.2 Hz, Ar); 6.70 (d, 1H, J=8.4 Hz, Ar); 7.16-7.19 (m, 1H, Ar); 7.30 (dd, 1H, J=2.0, 8.4 Hz, Ar); 7.38-7.48 (m, 3H, Ar); 8.21 (dd, 1H, J=2.2, 7.2 Hz, Ar); 8.34 (dd, 1H, J=2.2, 7.2 Hz, Ar); 9.66 (br t, 1H, J=5.8 NH); 9.74 (br s, 1H, NH); 10.25 (br s, 1H, NH) ppm. $^{13}$C-NMR (101 MHz, DMSO-$d_6$): δ 176.23; 170.15; 162.98; 161.23; 150.31; 147.87; 143.40; 142.92; 139.06; 134.21; 133.38; 125.90; 124.85; 120.49; 118.42; 117.70; 117.20; 116.46; 108.73; 106.60; 51.26; 38.29; 36.01; 33.85; 25.41 ppm. $^{19}$F-NMR (376 MHz, DMSO-$d_6$): δ −138.23 (d, 1F, J=22 Hz); −139.82 (d, 1F, J=24 Hz) ppm. Anal. Calcd for $C_{25}H_{22}N_4O_4F_2$: C, 62.50%; H, 4.62%; N, 11.66%; Found: C, 62.32%; H, 4.79%; N, 11.81%.

Synthesis of 1-(3,4-difluorobenzyl)-2-oxo-N-(2-oxo-2-((2-oxoindolin-5-yl)amino)ethyl)-1,2-dihydropyridine-3-carboxamide (IB32)

Starting from carboxylic acid 3 (154 mg, 0.58 mmol) and the 2-oxo-2-((2-oxoindolin-5-yl)amino)ethanaminium 2,2,2-trifluoro-acetate (0.58 mmol), the amide derivative was synthetized, using TBTU (187 mg, 0.58 mmol) as condensing agent. The procedure followed is the same described for derivative SST143 in above example 1.

The crude product was purified by column chromatography over silica gel using $CHCl_3$/MeOH 92:8 as the eluent to obtain the product as a white solid (63 mg, 0.14 mmol, 25% yield).

mp: 257-262° C. $^1$H-NMR (400 MHz, DMSO-$d_6$): δ 3.45 (s, 2H, $CH_2$ indole); 4.13 (d, 2H, J=5.2 Hz, $CH_2$ glycine); 5.23 (s, 2H, $CH_2$); 6.58 (t, 1H, J=6.9 Hz, Ar); 6.74 (d, 1H, J=8.4 Hz, Ar); 7.19-7.22 (m, 1H, Ar); 7.33 (dd, 1H, J=2.0, 8.4 Hz, Ar); 7.40-7.50 (m, 3H, Ar); 8.25 (dd, 1H, J=2.1, 6.9 Hz, Ar); 8.35 (dd, 1H, J=2.1, 6.9 Hz, Ar); 9.94 (br s, 1H, NH); 9.99 (t, 1H, J=5.2 Hz, NH); 10.28 (br s, 1H, NH) ppm. $^{13}$C-NMR (101 MHz, DMSO-$d_6$): δ 176.17, 166.69, 163.04, 161.09, 150.22, 147.83, 143.48, 143.19, 139.33, 134.18, 132.82, 126.05, 124.89, 120.20, 118.48, 117.65, 117.23, 116.44, 108.81, 106.45, 51.34, 43.05, 35.97 ppm. $^{19}$F-NMR (376 MHz; DMSO-$d_6$): δ −138.27 (d, 1F, J=24 Hz); −139.80 (d, 1F, J=24 Hz) ppm. Anal. Calcd for $C_{23}H_{18}N_4O_4F_2$: C, 61.06%; H, 4.01%; N, 12.38%; Found: C, 61.22%; H, 4.00%; N, 12.51%.

General Procedure to Synthesize Compounds IB35, IB36, SA16, SA23, DD21-23, DD25, DF8, DF9

To a solution of 2-oxo-indole derivative (0.12 mmol) dissolved in iPrOH/DMF or absolute EtOH (5 mL), was added the appropriate carbaldehyde (0.12 mmol) and a catalytic amount of piperidine. The resulting solution was stirred and heated to reach 110° C. for 4 h, then the solution was evaporated to dryness. The residual material was purified by crystallization.

(E/Z)-1-(3,4-difluorobenzyl)-2-oxo-N-(2-oxo-2-((2-oxo-3-(thiophe-2-ylmethylene)indolin-5-yl)amino)ethyl)-1,2-dihydropyridine-3-carboxamide (IB36)

The residual material was purified by crystallization from iPrOH, affording the final product as an orange solid consisting in a 1:2 E/Z isomeric mixture (35 mg, 0.06 mmol, 53% yield). mp: 223-227° C. $^1$H-NMR (400 MHz, DMSO-$d_6$): δ 4.17 (d, 2H, J=4.8 Hz, $CH_2$ glycine); 5.24 (s, 2H, $CH_2$); 6.59 (t, 1H, J=7.0 Hz, Ar); 6.80 (d, 0.66H, J=8.4 Hz, Ar); 6.85 (d, 0.33H, J=8.4 Hz, Ar); 7.17-7.23 (m, 2H, Ar); 7.31-7.33 (m, 0.33H, Ar); 7.40-7.50 (m, 2.66H, Ar); 7.78 (s, 0.33H, E-isomer, Ar); 7.82 (d, 0.33H, J=3.6 Hz, Ar, E-isomer); 7.89 (d, 0.66H, J=4.8 Hz, Ar, Z-isomer); 7.98-8.00 (m, 1.32H, Ar, Z-isomer); 8.03-8.05 (m, 1H, Ar, E+Z-isomers); 8.26-8.28 (m, 1H, Ar, E+Z-isomers); 8.36-8.39 (m, 1H, Ar, E+Z-isomers); 8.58 (s, 0.33H, C4, J=1.6 Hz Ar, E-isomer); 9.99-10.05 (m, 1.66H, NH); 10.11 (br s, 0.33H, NH); 10.55 (br s, 1H, NH) ppm. $^{13}$C-NMR (DMSO-$d_6$): δ 169.27, 167.41, 166.95, 166.89 163.12, 161.15, 150.41, 147.90, 138.46, 138.16, 137.23, 137.12, 136.58, 136.03, 134.57, 134.26, 132.88, 132.64, 132.19, 128.73, 128.26, 127.40, 124.93, 124.31, 123.54, 121.69, 121.06, 120.75, 120.29, 117.73, 117.28, 115.08, 111.59, 109.65, 106.54, 51.45, 43.08 ppm. $^{19}$F-NMR (376 MHz; DMSO-$d_6$): δ −138.24 (d, 1F, J=24 Hz); −139.76 (d, 0.33F, J=24 Hz), −139.79 (d, 0.66F, J=24 Hz) ppm. Anal. Calcd for $C_{28}H_{20}N_4O_4F_2S$: C, 61.53%; H, 3.69%; N, 10.25%; Found: C, 61.62%; H, 3.63%; N, 10.39%.

(Z)—N-(2-((3-((1H-imidazol-5-yl)methylene)-2-oxoindolin-5-yl)amino)-2-oxoethyl)-1-(3,4-difluorobenzyl)-2-oxo-1,2-dihydro pyridine-3-carboxamide (IB35)

The residual material was purified by crystallization from iPrOH, affording the Z-isomer as a yellow solid (32 mg, 0.06 mmol, 52% yield). mp: 230-235° C. $^1$H-NMR (400 MHz, DMSO-$d_6$): δ 4.17 (d, 2H, J=4.4 Hz, $CH_2$ glycine); 5.24 (s, 2H, $CH_2$); 6.60 (t, 1H, J=6.9 Hz, Ar); 6.85 (d, 1H, J=8.8 Hz, Ar); 7.19-7.21 (m, 2H, Ar); 7.43-7.50 (m, 3H, Ar); 7.71 (s, 1H, Ar); 7.75 (s, 1H, Ar); 8.01 (s, 1H, Ar); 8.05 (s, 1H, Ar); 8.27 (dd, 1H, J=2.0, 6.9 Hz, Ar); 8.37 (d, 1H, J=2.0, 6.9 Hz, Ar); 10.61 (br s, 2H, NH); 10.95 (br s, 1H, NH) ppm. $^{13}$C-NMR (101 MHz, DMSO-$d_6$): δ 169.05, 166.93, 163.12, 161.16, 150.41, 147.90, 143.57, 143.31, 139.62, 138.85, 135.79, 134.32, 133.20, 128.07, 124.93, 124.47, 122.90, 120.25, 120.10, 119.67, 117.73, 117.23, 111.17, 109.86, 106.52, 51.45, 43.14 ppm. $^{19}$F-NMR (376 MHz; DMSO-$d_6$): δ −138.25 (d, 1F, J=24 Hz); −139.80 (d, 1F, J=24 Hz) ppm. Anal. Calcd for $C_{27}H_{20}N_6O_4F_2$: C, 61.13%; H, 3.80%; N, 15.84%; Found: C, 61.15%; H, 4.03%; N, 15.89%.

(Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide (SA16)

The residual material was purified by crystallization from EtOH, affording the Z-isomer as a yellow solid (41 mg, 0.07 mmol, 57% yield). mp: 248-255° C. $^1$H-NMR (400 MHz, DMSO-$d_6$): δ 5.20-5.31 (m, 2H, $CH_2$); 5.81 (d, 1H, J=7.2 Hz, $CH_2$); 6.60 (t, 1H, J=6.8 Hz, Ar); 6.83 (d, 1H, J=8.0 Hz, Ar); 7.19-7.21 (m, 2H, Ar); 7.29-7.52 (m, 8H, Ar); 7.71 (s, 1H, Ar); 7.78 (s, 1H, Ar); 8.01 (s, 1H, Ar); 8.04 (s, 1H, Ar); 8.27 (dd, 1H, J=2.0, 6.8 Hz, Ar); 8.35 (dd, 1H, J=2.0, 6.8 Hz, Ar); 10.46 (br s, 1H, NH); 10.72 (d, 1H, J=7.2 Hz, NH); 10.97 (br s, 1H, NH) ppm. $^{13}$C-NMR (101 MHz, DMSO-d$_6$): δ 169.03, 167.95, 162.32, 161.30, 150.35, 147.91, 143.82, 143.57, 139.68, 138.95, 138.72, 136.04, 134.24, 132.92, 128.70, 128.07, 127.89, 126.83, 124.87, 124.51, 123.16, 119.90, 119.77, 117.79, 117.15, 111.16, 109.88, 106.68, 57.06, 51.36 ppm. Anal. Calcd for $C_{33}H_{24}N_6O_4F_2$: C, 65.34%; H, 3.99%; N, 13.85%; Found: C, 65.25%; H, 4.03%; N, 13.79%.

(Z)—(R)—N-(2-((3-((1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide (SA23)

The residual material was purified by crystallization from EtOH, affording the yellow solid as the Z-isomer, which slowly interconverts in 2:1 E/Z mixture (45 mg, 0.07 mmol, 62% yield). mp: 304-307° C. $^1$H-NMR (400 MHz, DMSO-d$_6$) [t=0]: δ 5.20-5.30 (m, 2H, CH$_2$); 5.81 (d, 1H, J=7.2 Hz, CH$_2$); 6.60 (t, 1H, J=7.0 Hz, Ar); 6.86 (d, 1H, J=8.4 Hz, Ar); 7.17-7.20 (m, 1H, Ar); 7.21-7.56 (m, 11H, Ar); 7.58 (s, 1H, CH=); 7.86 (d, 1H, J=2.0 Hz, C4, Ar); 8.26 (dd, J=2.0, 7.0 Hz, 1H, Ar); 8.36 (dd, J=2.0, 7.0 Hz, 1H, Ar); 10.45 (br s, 1H, NH); 10.68 (d, 1H, J=7.2 Hz, NH); 11.11 (br s, 1H, NH) ppm. $^{19}$F-NMR (376 MHz; DMSO-d6) [t=0]: δ −138.14 (d, 1F, J=24 Hz); −139.76 (d, 1F, J=24 Hz) ppm. $^{13}$C-NMR (101 MHz, DMSO-d$_6$) [t=12 h]: δ 169.50 (Z-isomer), 168.89 (E-isomer), 168.01, 162.31, 162.25, 161.26, 150.46, 147.44, 143.78 (E-isomer), 143.50 (Z-isomer), 143.35 (E-isomer), 142.89 (Z-isomer), 138.92 (Z-isomer), 138.86 (Z-isomer), 138.56 (E-isomer), 136.23 (E-isomer), 134.16, 133.09, 132.62, 132.11, 128.68 (E-isomer), 128.60 (Z-isomer), 127.87 (E-isomer), 127.77 (Z-isomer), 126.85, 124.85, 124.31, 123.95, 123.42, 122.36, 121.90, 120.91 (Z-isomer), 120.79 (E-isomer), 119.93 (Z-isomer), 119.86 (E-isomer), 117.74, 117.16, 111.74, 110.06, 108.85, 106.65, 57.06, 51.28 ppm. $^{19}$F-NMR (376 MHz; DMSO-d6) [t=24 h]: δ −138.14 (d, 0.33F, J=24 Hz, Z-isomer); −138.16 (d, 0.66F, J=24 Hz, E-isomer); −139.76 (d, 0.33F, J=24 Hz, Z-isomer); −139.79 (d, 0.66F, J=24 Hz, E-isomer) ppm. Anal. Calcd for $C_{33}H_{24}N_6O_4F_2$: C, 65.34%; H, 3.99%; N, 13.85%; Found: C, 65.25%; H, 4.03%; N, 13.79%.

(E/Z)-1-(3,4-difluorobenzyl)-2-oxo-N-(3-oxo-3-((2-oxo-3-(thiophen-2-ylmethylene)indolin-5-yl)amino)propyl)-1,2-dihydropyridine-3-carboxamide (DD22)

The residual material was purified by crystallization from iPrOH. $^1$H-NMR (400 MHz, DMSO-d$_6$): δ 2.57-2.59 (m, 2H, CH$_2$); 3.57-3.61 (m, 2H, CH$_2$); 5.22 (s, 2H, CH$_2$ benzylic); 6.57 (t, 1H, J=6.8 Hz, Ar); 6.78 (d, 0.75H, J=8.4 Hz, Ar); 6.81 (d, 0.25H, J=8.4 Hz, Ar); 7.15-7.22 (m, 3H, Ar); 7.31-7.44 (m, 2H, Ar); 7.76 (s, 0.25H, E-isomer, Ar); 7.89 (d, 0.90H, J=3.2 Hz, Ar, Z-isomer); 7.96-8.00 (m, 3H, Ar, E+Z-isomer); 8.19-8.21 (m, 1H, Ar, E+Z-isomer); 8.35-8.38 (m, 1H, Ar, E+Z-isomer); 8.58 (s, 0.11H, C4, J=1.6 Hz Ar, E-isomer); 9.79 (br s, 1H, NH); 9.87 (m, 0.80H, NH); 9.95 (m, 0.20H, NH); 10.52 (br s, 0.35H, NH); 10.55 (br s, 1H, NH) ppm.

(Z/E)-N-(3-((3-((1H-imidazol-2-yl)methylene)-2-oxoindolin-5-yl)amino)-3-oxopropyl)-1-(3,4-difluorobenzyl)-2-oxo-1,2-dihydropyridine-3-carboxamide (mix 88:12=Z:E) (DD25)

1H-NMR (400 MHz, DMSO-d6): δ 2.58 (t, 2H, J=6.4 Hz, CH$_2$); 3.59 (q, 2H, J=6.4 Hz, CH2); 4.17 (d, 2H, J=4.4 Hz, CH$_2$); 5.20 (s, 2H, CH$_2$); 6.57 (t, 1H, J=6.8 Hz, Ar); 6.82 (d, 1H, J=8.4 Hz, Ar); 7.12-7.14 (m, 1H, Ar); 7.33-7.43 (m, 4H, Ar); 7.52 (s, 1H, Ar); 7.56 (s, 1H, Ar); 7.92 (s, 1H, Ar); 8.19 (dd, 1H, J=2.0, 6.8 Hz, Ar); 8.35 (dd, 1H, J=2.0, 6.8 Hz, Ar); 9.81 (br s, 1H, NH); 9.91 (s, 1H, NH); 11.08 (br s, 1H, NH) ppm.

(Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide (DD21)

1H-NMR (400 MHz, DMSO-d6): δ 2.59 (br m, 2H, CH$_2$); 3.57-3.61 (m, 2H, CH$_2$); 5.19 (s, 2H, CH$_2$); 6.57 (t, 1H, J=6.8 Hz, Ar); 6.82 (d, 1H, J=8.0 Hz, Ar); 7.14-7.21 (m, 2H, Ar); 7.33-7.45 (m, 2H, Ar); 7.71 (s, 1H, Ar); 8.01 (s, 1H, Ar); 8.19 (d, 1H, J=6.0 Hz, Ar); 8.36 (d, 1H, J=6.0 Hz, Ar); 9.80 (br s, 1H, NH); 9.90 (br s, 1H, NH); 10.93 (br s, 1H, NH) ppm.

(Z)-1-(3,4-difluorobenzyl)-N-(3-((3-(4-fluorobenzylidene)-2-oxoindolin-5-yl)amino)-3-oxopropyl)-2-oxo-1,2-dihydropyridine-3-carboxamide (DD23)

$^1$H-NMR (400 MHz, DMSO-d$_6$): δ 2.50-2.53 (m, 2H, CH$_2$); 3.53-3.55 (m, 2H, CH$_2$); 5.18 (s, 2H, CH$_2$ benzylic); 6.56 (t, 1H, J=7.2 Hz, Ar); 6.80 (d, 1H, J=8.4 Hz, Ar); 7.10-7.16 (m, 1H, Ar); 7.32-7.44 (m, 5H, Ar); 7.58 (s, 1H, CH=); 7.76-7.80 (m, 2H, Ar); 7.98 (s, 1H, C4 Ar); 8.20 (d, 1H, J=6.4 Hz, Ar); 8.34 (d, 1H, J=6.4 Hz, Ar); 9.78-9.82 (m, 2H, NH); 10.53 (br s, 1H, NH) ppm.

(Z)—N-(4-((3-((1H-imidazol-5-yl)methylene)-2-oxoindolin-5-yl)amino)-4-oxobutyl)-5-(3,4-difluorobenzyl)-6-oxocyclohexa-1,3-diene-1-carboxamide (DF8)

To a solution of 2-oxo-indole derivative 7 (70 mg, 0.15 mmol) dissolved in iPrOH/DMF, was added the 4-imidazole-carbaldehyde (14 mg, 0.15 mmol) and a catalytic amount of piperidine. The procedure followed is the same described for derivative IB35. The residual material was purified by crystallization from iPrOH, affording the Z isomer as an orange solid (44 mg, 0.08 mmol, 66% yield). Mp: 240-244° C. $^1$H NMR (400 MHz, DMSO-d$_6$): δ: 1.80-1.85 (m, 2H, CH$_2$); 2.34 (t, 2H, J=7.2 Hz, CH$_2$); 3.35-3.39 (m, 2H, CH$_2$); 5.19 (s, 2H, CH$_2$); 6.57 (t, 1H, J=7.0 Hz, Ar); 6.80 (d, 1H, J=8.4 Hz, Ar); 7.18-7.21 (m, 2H, Ar); 7.38-7.46 (m, 2H, Ar); 7.65-7.75 (m, 2H, Ar); 7.95-8.05 (m, 2H, Ar); 8.20 (dd, 1H, J=1.8, 7.0 Hz, Ar); 8.35 (dd, 1H, J=1.8, 7.0 Hz, Ar); 9.68 (br t, 1H, J=5.6 Hz, NH); 9.84 (br s, 1H, NH); 10.89 (br s, 1H, NH) ppm. $^{13}$C-NMR (101 MHz, DMSO-d6): δ 170.33; 169.04; 162.99; 161.24; 150.05; 147.87; 143.41; 142.91; 139.52; 138.73; 134.20; 133.68; 124.85; 124.30; 122.70; 120.50; 120.20; 119.77; 117.70; 117.20; 111.22; 109.70; 106.60; 51.27; 38.31; 33.79; 25.38 ppm. $^{19}$F-NMR (376 MHz, DMSO-d$_6$): δ: −138.22 (d, 1F, J=24 Hz); − 139.81 (d, 1F, J=24 Hz) ppm. Anal. Calcd for $C_{29}H_{24}N_6O_4F_2$: C, 62.36%; H, 4.33%; N, 15.05%; Found: C, 62.66%; H, 4.21%; N, 15.39%.

(E/Z)-1-(3,4-difluorobenzyl)-2-oxo-N-(4-oxo-4-((2-oxo-3-(thiophen-2-ylmethylene)indolin-5-yl)amino)butyl)-1,2-dihydropyridine-3-carboxamide (DF9)

To a solution of 2-oxo-indole derivative 7 (70 mg, 0.15 mmol) dissolved in iPrOH/DMF, was added the 2-thiophenecarbaldehyde (17 mg, 0.15 mmol) and a catalytic amount of piperidine. The procedure followed is the same described for derivative IB35. The residual material was purified by crystallization from iPrOH affording the final product as an orange solid consisting in a 40:60 E/Z isomeric mixture (52 mg, 0.09 mmol, 76% yield). Mp: 189-194° C. $^1$H NMR (400 MHz, DMSO-$d_6$): δ 1.80-1.87 (m, 2H, $CH_2$); 2.32-2.36 (m, 2H, $CH_2$); 3.35-3.39 (m, 2H, $CH_2$); 5.19 (m, 2H, $CH_2$); 6.54-6.59 (m, 1H, Ar); 6.77 (d, 0.60H, J=8.0 Hz, Ar, Z isomer); 6.81 (d, 0.40H, J=8.4 Hz, Ar, E isomer); 7.18-7.23 (m, 2.20H, Ar); 7.31-7.32 (m, 0.40H, Ar, E isomer); 7.40-7.47 (m, 2.40H, Ar); 7.76 (s, 0.40H, Ar, E isomer); 7.81-7.88 (m, 1H, Ar, E/Z isomer); 7.96-7.99 (m, 1.60H, Ar), 8.03 (m, 0.60H, Ar, Z isomer); 8.20-8.22 (m, 1H, Ar); 8.33-8.37 (m, 1H, Ar); 8.61 (m, 0.40H, Ar, E isomer); 9.67-9.69 (br m, 1H, NH); 9.82 (br s, 0.60H, NH, Z isomer); 9.90 (br s, 0.40H, NH, E isomer); 10.51 (br s, 1H, NH) ppm. $^{13}$C-NMR (101 MHz, DMSO-$d_6$): δ 170.32 (Z isomer); 169.31 (E isomer); 167.43; 163.02; 161.26; 150.34; 148.09; 143.45 (Z isomer); 142.97 (E isomer); 138.19 (E isomer); 138.04 (Z isomer); 137.23 (Z isomer); 137.18 (E isomer); 136.39 (Z isomer); 135.89 (E isomer); 134.48; 134.23; 133.39 (E isomer); 133.14 (Z isomer); 132.17; 128.70 (Z isomer); 128.08 (E isomer); 127.41 (Z isomer); 127.19 (E isomer); 124.88; 124.17 (Z isomer); 123.63 (E isomer); 121.81; 120.95; 120.65; 120.50; 120.44; 117.74; 117.23; 115.14; 111.65; 109.68 (E isomer); 109.34 (Z isomer); 106.50; 51.31; 38.34; 33.96 (E isomer); 33.77 (Z isomer); 25.42 ppm. $^{19}$F-NMR (376 MHz, DMSO-$d_6$): δ −139.22 (d, 1F, J=24 Hz); −139.81 (d, 1F, J=24 Hz) ppm. Anal. Calcd for $C_{30}H_{24}N_4O_4F_2S$: C, 62.71%; H, 4.21%; N, 9.75%; Found: C, 63.89%; H, 4.01%; N, 9.55%.

Preparation of Compounds DD40 and DD41

The compounds DD40 and DD41 were prepared by following Scheme 3

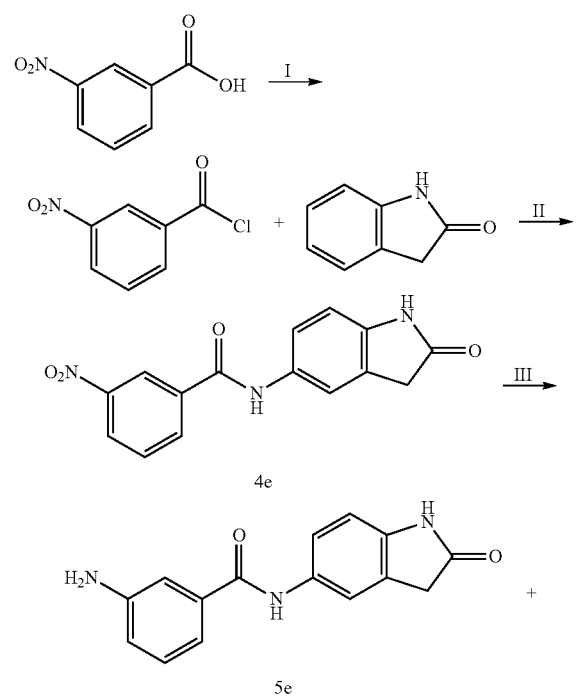

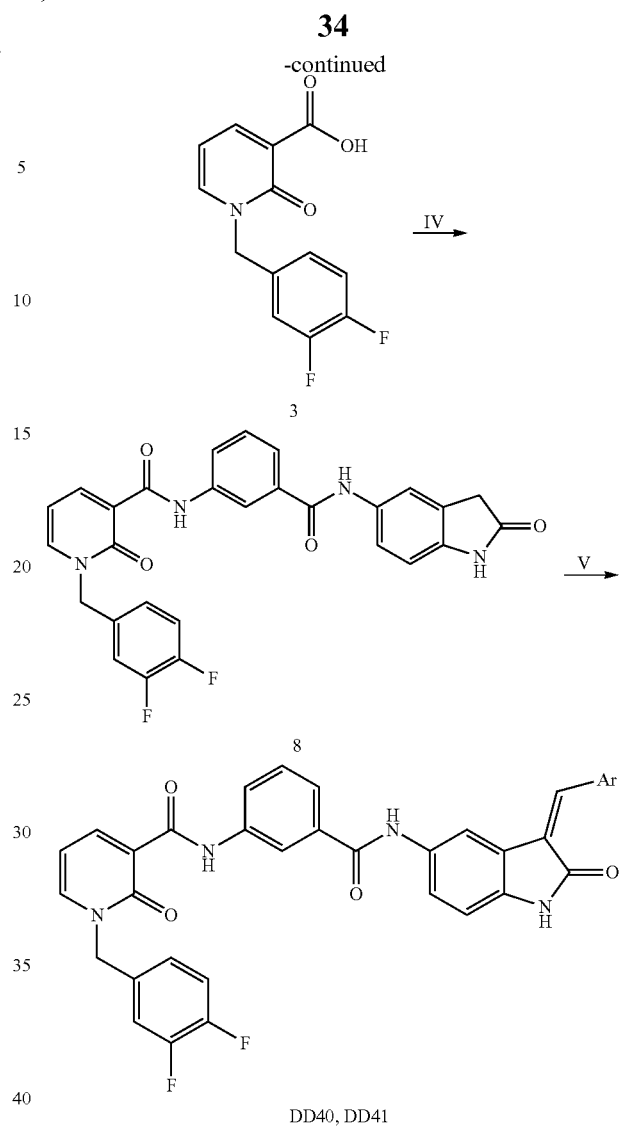

DD40, DD41

Reagents and Conditions: I. $SOCl_2$, 82° C., 12 h; II. Pyridine, 3 h; III. $H_2$, Pd/C, EtOH; IV. TBTU, DIPEA, dry DMF, r.t., 16 h; V) Carboxyaldehyde, Piperidine, EtOH, reflux 110° C., 4 h.

3-nitrobenzoyl Chloride 3-nitrobenzoic acid (600 mg, 3.59 mmol) and thionyl chloride (0.26 mL, 3.59 mmol) were reacted under $N_2$ atmosphere at 82° C. for 16 h. Once TLC verified the disappearance of the precursor, the solution was evaporated to dryness and the crude product was immediately/directly used for the next step without further purification.

3-nitro-N-(2-oxoindolin-5-yl)benzamide (4e)

To a mixture of nitrobenzoylchloride (3.59 mmol) in pyridine was added the 5-amino-2-oxindole (379 mg, 2.56 mmol). Mixture was stirred at room temperature for 3 h and poured into ice water. The precipitate was filtered, washed with water and dried in vacuum to give final product as white powder (544.1 mg, 1.83 mmol, 71% yield). $^1$H-NMR (400 MHz, DMSO-$d_6$): δ 3.51 (s, 2H, $CH_2$); 6.81 (d, 1H, J=8.4 Hz, Ar); 7.52 (d, 1H, J=8.4 Hz, Ar); 7.66 (s, 1H, Ar); 7.83 (t, 1H, J=8.0 Hz, Ar); 8.37-8.43 (m, 2H, Ar); 8.77 (s, 1H, Ar); 10.35 (br s, 1H, NH); 10.45 (br s, 1H, NH) ppm.

Anal. Calcd for $C_{15}H_{11}N_3O_4$: C, 60.61%; H, 3.73%; N, 14.14%; Found: C, 60.78%; H, 3.86%; N, 14.05%.

3-((2-oxoindolin-5-yl)carbamoyl)benzenaminium Chloride (5e)

Derivative 4e (544 mg, 1.83 mmol) dissolved in absolute EtOH (70 mL) was hydrogenated in the presence of 10% Pd—C for 4 h at rt. Then the catalyst was filtered off through Celite, the Celite rinsed with additional EtOH and the solution was evaporated, to give 5e as a brown solid. Crude product was transformed in the correspondent hydrochloridric salt (171.5 mg, 0.57 mmol, 31% yield). $^1$H-NMR (400 MHz, $CD_3OD$): δ 3.55 (s, 2H, $CH_2$); 6.90 (d, 1H, J=8.4 Hz, Ar); 7.49 (dd, 1H, J=1.8, 8.4 Hz, Ar); 7.59-7.62 (m, 2H, Ar); 7.70 (t, 1H, J=8.0 Hz, Ar); 7.95 (d, 1H, J=1.8, Ar); 8.05 (d, 1H, J=8.0 Hz, Ar) ppm. Anal. Calcd for $C_{15}H_{14}N_3O_2Cl$: C, 59.51%; H, 4.33%; N, 13.88%; Found: C, 59.78%; H, 4.47%; N, 13.90%.

1-(3,4-difluorobenzyl)-2-oxo-N-(3-((2-oxoindolin-5-yl)carbamoyl)phenyl)-1,2-dihydropyridine-3-carboxamide (8)

Carboxylic acid 3 (175 mg, 0.66 mmol) was reacted with amine derivative 5e (200 mg, 0.66 mmol) in dry DMF (4 mL). Reaction was conducted in presence of TBTU (212 mg, 0.66 mmol) and DIPEA (4 mL) as previously reported for compound SST143. Then the organic solvent was evaporated under vacuum and the crude product was purified by flash chromatography over silica gel, using $CHCl_3$/MeOH (97:3) as the eluent, yielding pure 8 as a white solid (80 mg, 0.16 mmol, 24% yield). $^1$H-NMR (400 MHz, DMSO-$d_6$): δ 3.50 (s, 2H, $CH_2$); 5.31 (s, 2H, $CH_2$); 6.71 (t, 1H, J=7.0 Hz, Ar); 6.79 (d, 1H, J=8.4 Hz, Ar); 7.22-7.24 (m, 1H, Ar); 7.41-7.52 (m, 4H); 7.66-7.68 (m, 2H, Ar); 8.00 (d, 1H, J=8.4 Hz, Ar); 8.13 (s, 1H, Ar); 8.33 (dd, 1H, J=2.0, 7.0 Hz, Ar); 8.51 (dd, 1H, J=2.0, 7.0 Hz, Ar); 10.15 (br s, 1H, NH); 10.32 (br s, 1H, NH); 12.14 (br s, 1H, NH) ppm. $^{13}$C-NMR (101 MHz, DMSO-$d_6$): δ 176.30, 164.75, 161.60, 161.45, 150.37, 147.92, 144.29, 143.91, 139.77, 138.28, 135.92, 134.02, 133.03, 129.07, 125.90, 124.84, 122.94, 122.48, 120.01, 118.82, 117.83, 117.67, 117.27, 117.09, 108.74, 107.34, 51.52, 36.03 ppm. $^{19}$F-NMR (376 MHz, DMSO-$d_6$): δ −138.12 (d, 1F, J=24 Hz, Ar); −139.73 (d, 1F, J=24 Hz, Ar) ppm. Anal. Calcd for $C_{28}H_{20}N_4O_4F_2$: C, 65.37%; H, 3.92%; N, 10.89%; Found: C, 65.69%; H, 3.79%; N, 10.93%.

(Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide (DD40)

To a solution of derivative 8 (40 mg, 0.08 mmol) in iPrOH/DMF was added the 4-imidazolecarbaldehyde (8 mg, 0.08 mmol) and a catalytic amount of piperidine. The procedure followed is the same described for derivative IB35. The residual material was purified by crystallization from iPrOH affording the yellow solid as the Z isomer (15 mg, 0.03 mmol, 37% yield). M.p.: 326-330° C.; $^1$H-NMR (400 MHz, DMSO-$d_6$): δ 5.31 (s, 2H, $CH_2$); 6.71 (t, 1H, J=6.8 Hz, Ar); 6.89 (d, 1H, J=8.4 Hz, Ar); 7.22-7.24 (m, 1H, Ar); 7.41-7.54 (m, 4H, Ar); 7.71 (d, 1H, J=8.0 Hz, Ar); 7.75-7.77 (m, 2H, Ar); 8.01-8.03 (m, 2H, Ar); 8.10 (s, 1H, Ar); 8.18 (s, 1H, Ar); 8.33 (dd, 1H, J=2.0, 6.8 Hz, Ar); 8.52 (dd, 1H, J=2.0, 6.8 Hz, Ar); 10.25 (br s, 1H, NH); 12.16 (br s, 1H, NH) ppm. $^{13}$C-NMR (101 MHz, DMSO-$d_6$): δ 164.84, 161.60, 161.46, 150.36, 147.85, 144.29, 143.91, 138.30, 136.21, 135.78, 134.02, 133.24, 129.11, 128.07, 124.81, 124.35, 122.94, 122.55, 121.36, 120.02, 118.82, 117.75, 117.16, 112.80, 109.65, 107.34, 51.52 ppm. $^{19}$F-NMR (376 MHz, DMSO-$d_6$): δ −138.12 (d, 1F, J=24 Hz, Ar); −139.73 (d, 1F, J=24 Hz, Ar) ppm. Anal. Calcd for $C_{32}H_{22}N_6O_4F_2$: C, 64.86%; H, 3.74%; N, 14.18%; Found: C, 65.08%; H, 3.77%; N, 14.39%.

(E/Z)-1-(3,4-difluorobenzyl)-2-oxo-N-(3-((2-oxo-3-(thiophen-2-ylmethylene)indolin-5-yl)carbamoyl)phenyl)-1,2-dihydropyridine-3-carboxamide (DD41)

To a solution of 2-oxo-indole derivative 8 (40 mg, 0.08 mmol) dissolved in iPrOH/DMF, was added the 2-thiophenecarbaldehyde (9 mg, 0.08 mmol) and a catalytic amount of piperidine. The procedure followed is the same described for derivative IB35. The residual material was purified by crystallization from iPrOH, affording the final product (12 mg, 0.02 mmol, 25% yield) as an orange solid consisting in a mixture of E/Z isomers (1:4). M.p.: 295-298° C.; $^1$H-NMR (400 MHz, DMSO-$d_6$): δ 5.32 (s, 2H, $CH_2$); 6.71-6.73 (m, 1H, Ar); 6.86-6.88 (m, 1H, Ar); 7.23-7.34 (m, 2H, Ar); 7.44-7.52 (m, 3.75H, Ar); 7.62-8.20 (m, 7H, Ar); 8.34 (s, 1H, Ar); 8.53 (s, 1H, Ar); 8.78 (s, 0.25H, Ar, E isomer); 10.25-10.33 (br m, 1H, NH); 10.60 (br s, 1H, NH); 12.17 (br s, 1H, NH) ppm. $^{13}$C-NMR (101 MHz, DMSO-$d_6$): δ 169.35 (E isomer), 167.45 (Z isomer), 164.97 (E isomer), 164.80 (Z isomer), 161.62, 161.47, 150.37, 147.93, 144.30, 143.92, 138.86 (E isomer), 138.32 (Z isomer), 137.96 (E isomer), 137.25 (Z isomer), 137.01 (E isomer), 135.91, 134.48, 134.01, 132.94 (E isomer), 132.70 (Z isomer), 132.25 (E isomer), 129.12 (Z isomer), 128.69 (Z isomer), 128.20 (E isomer), 127.43 (Z isomer), 124.86, 124.22, 123.59 (E isomer), 123.02 (E isomer), 122.93 (Z isomer), 122.66 (E isomer), 122.55 (Z isomer), 122.04 (Z isomer), 121.74 (Z isomer), 120.64 (E isomer), 120.04 (Z isomer), 118.92 (E isomer), 118.83 (Z isomer), 117.78, 117.18, 116.57 (E isomer), 113.26 (Z isomer), 109.68 (E isomer), 109.27 (Z isomer), 106.50, 51.54 ppm. $^{19}$F-NMR (376 MHz, DMSO-$d_6$): δ −138.12 (d, 1F, J=24 Hz, Ar); −139.73 (d, 1F, J=24 Hz, Ar) ppm. Anal. Calcd for $C_{33}H_{22}N_4O_4F_2S$: C, 65.12%; H, 3.64%; N, 9.21%; Found: C, 65.38%; H, 3.69%; N, 9.28%.

Evaluation of the Compounds of Formulas (I) and (II)

The activity of the inhibitor compounds can be assayed utilizing methods known in the art and/or methods presented therein.

The compounds of Formula (I) and (II) were tested in the biological test named Kinase-specific Z'-LYTE® assay (Invitrogen Corporation, Life Technologies).

The compounds synthetized were hence subjected to FRET-based Z'-Lyte assay against PDK1 Direct kinase to evaluate the kinase inhibitory activities (Invitrogen).

Data indicate that the compounds JJ31, IB32, IB35, SA23, SA16, DD22, DD21, DD40, DF8 and DF9 displayed the best effects on PDK1 (>50% inhibition versus PDK1 at 10 uM). The IC50 values and percentage of Inhibition are reported in the following table.

| Compound | Structure | MW | PDK1 (%) inhibition at 10 μM or IC50 (nM) |
|---|---|---|---|
| JJ31 | 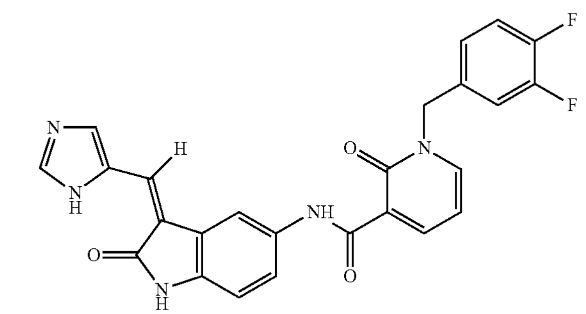 [SMILES: O=C1Nc2ccc(NC(=O)c3cccn(Cc4ccc(F)c(F)c4)c3=O)cc2/C1=C/c1cnc[nH]1] | 473.43 | 512 nM |
| IB32 | 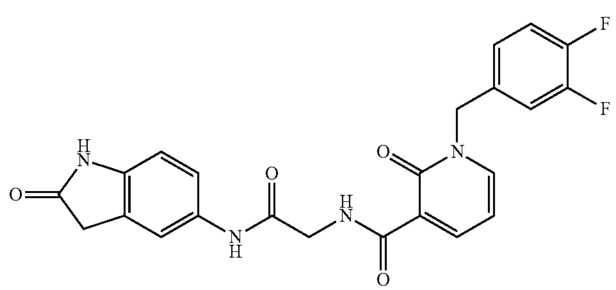 [SMILES: O=C(CNC(=O)c1cccn(Cc2ccc(F)c(F)c2)c1=O)Nc1ccc2c(c1)CC(=O)N2] | 452.13 | 6680 nM |
| IB36 | 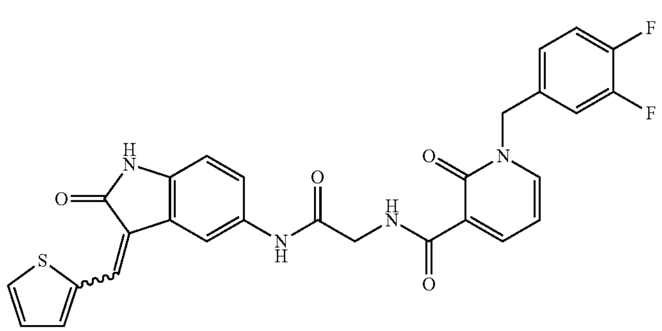 [SMILES: O=C(CNC(=O)c1cccn(Cc2ccc(F)c(F)c2)c1=O)Nc1ccc2c(c1)C(=Cc1cccs1)C(=O)N2] | 546.12 | 19% |
| IB35 | 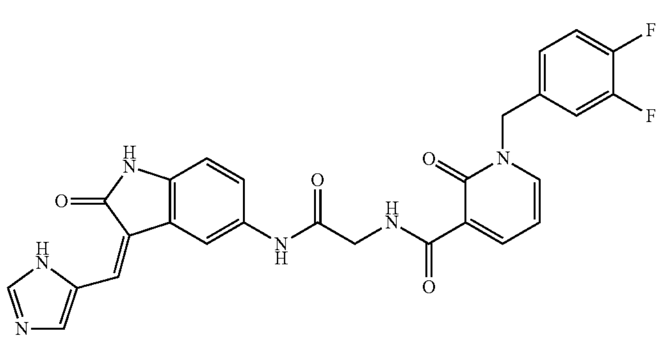 [SMILES: O=C(CNC(=O)c1cccn(Cc2ccc(F)c(F)c2)c1=O)Nc1ccc2c(c1)/C(=C/c1cnc[nH]1)C(=O)N2] | 530.15 | 112 nM |

-continued
| Compound | Structure | MW | PDK1 (%) inhibition at 10 μM or IC50 (nM) |
|---|---|---|---|
| SA16 | 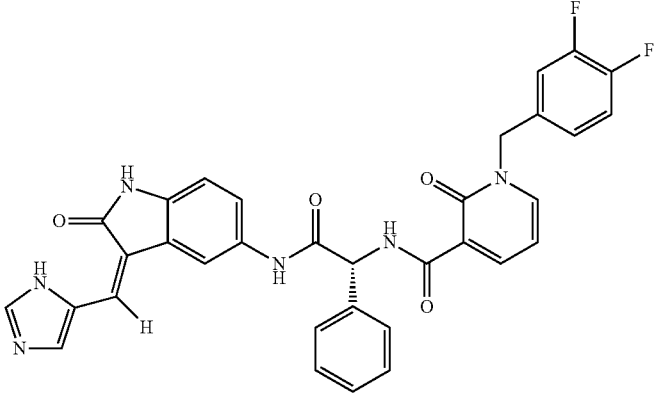 [SMILES: O=C1Nc2ccc(NC(=O)[C@H](NC(=O)c3cccn(Cc4ccc(F)c(F)c4)c3=O)c3ccccc3)cc2/C1=C/c1cnc[nH]1] | 606.58 | 416 nM |
| SA23 | 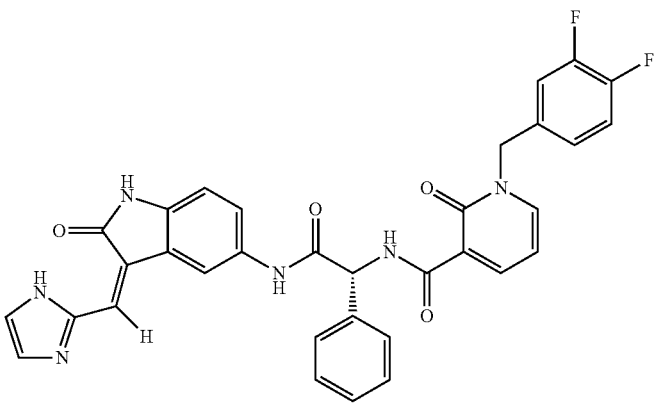 | 606.58 | 1520 nM |
| DD22 | 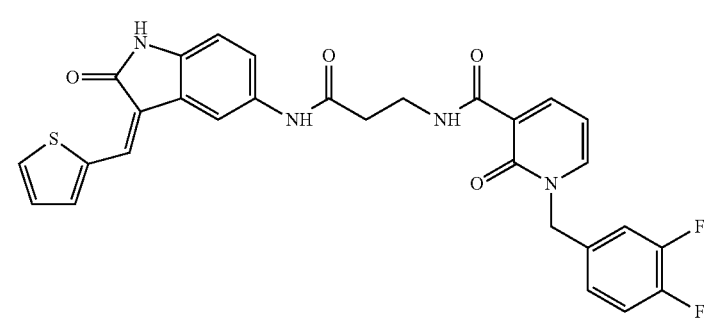 [SMILES: O=C(CCNC(=O)c1cccn(Cc2ccc(F)c(F)c2)c1=O)Nc1ccc2c(c1)/C(=C/c1cccs1)C(=O)N2] | 560.57 | 1340 nM |
| DD21 | 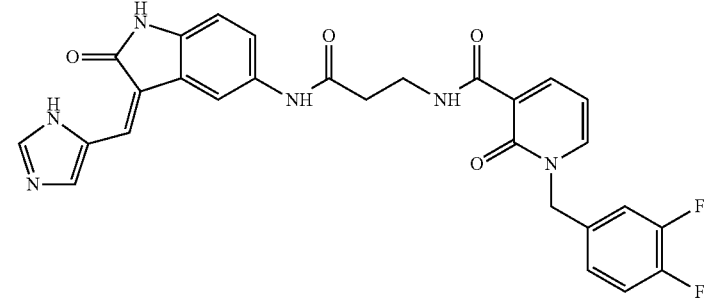 [SMILES: O=C(CCNC(=O)c1cccn(Cc2ccc(F)c(F)c2)c1=O)Nc1ccc2c(c1)/C(=C/c1cnc[nH]1)C(=O)N2] | 544.51 | 103 nM |

-continued

| Compound | Structure | MW | PDK1 (%) inhibition at 10 μM or IC50 (nM) |
|---|---|---|---|
| DD23 | 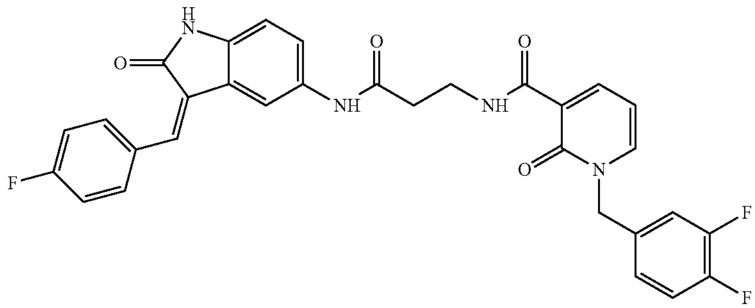 [SMILES: O=C(CCNC(=O)c1cccn(Cc2ccc(F)c(F)c2)c1=O)Nc1ccc2c(c1)/C(=C/c1ccc(F)cc1)C(=O)N2] | 572.53 | 15% |
| DD25 | 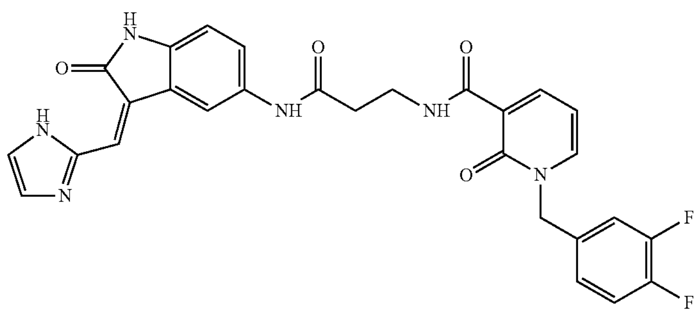 | 544.515 | 47% |
| DD40 | 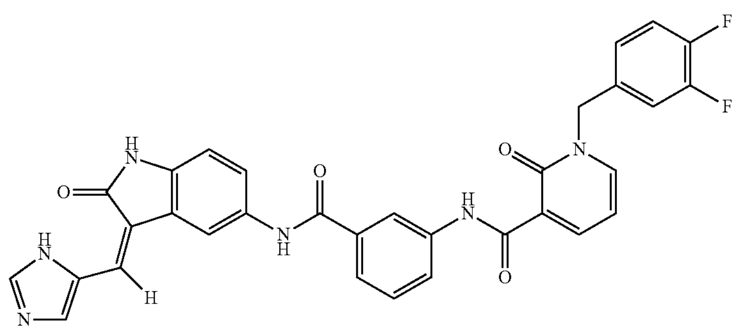 [SMILES: O=C1Nc2ccc(NC(=O)c3cccc(NC(=O)c4cccn(Cc5ccc(F)c(F)c5)c4=O)c3)cc2/C1=C/c1cnc[nH]1] | 592.56 | 245 nM |
| DD41 | 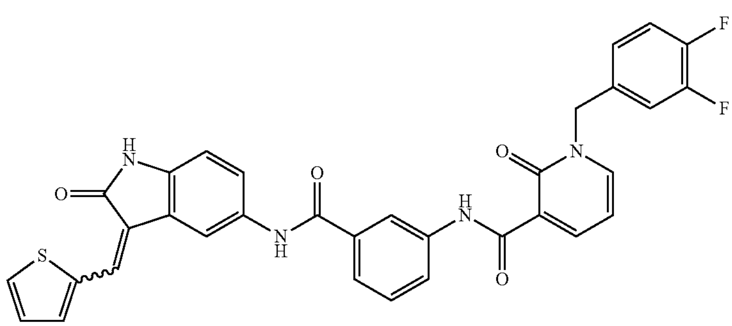 [SMILES: O=C1Nc2ccc(NC(=O)c3cccc(NC(=O)c4cccn(Cc5ccc(F)c(F)c5)c4=O)c3)cc2C1=Cc1cccs1] | 608.62 | 26% |

| Compound | Structure | MW | PDK1 (%) inhibition at 10 μM or IC50 (nM) |
|---|---|---|---|
| DF8 | 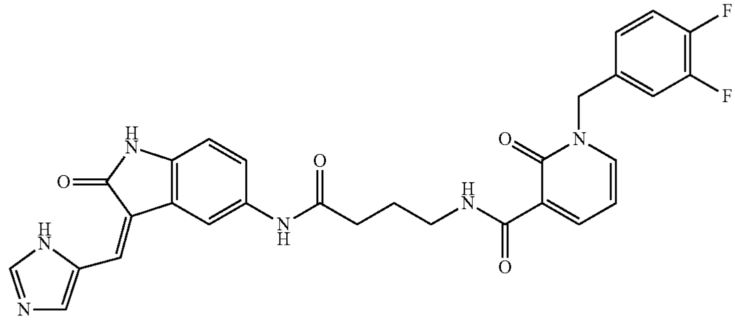 [SMILES: O=C(CCCNC(=O)c1cccn(Cc2ccc(F)c(F)c2)c1=O)Nc1ccc2c(c1)/C(=C/c1cnc[nH]1)C(=O)N2] | 558.55 | 245 nM |
| DF9 | 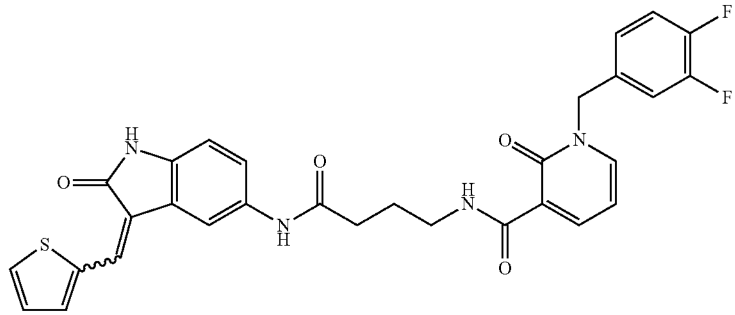 [SMILES: O=C(CCCNC(=O)c1cccn(Cc2ccc(F)c(F)c2)c1=O)Nc1ccc2c(c1)C(=Cc1cccs1)C(=O)N2] | 574.60 | 5880 nM |

Compound IB35 which showed an optimal inhibition of PDK1 was also tested for the selectivity by comparing its ability in inhibiting other kinases in the Akt pathway. The results are reported below

| Compound IB35 Conc (nM) | ATP | Kinase | Technology | % Inhibition 1 | % Inhibition 2 | % Inhibition Avg |
|---|---|---|---|---|---|---|
| 100 | Km app | CDK7/cyclin H/MNAT1 | Adapta | 2 | −1 | 1 |
| 100 | Km app | CDK9/cyclin T1 | Adapta | 7 | 5 | 6 |
| 100 | Km app | CHUK (IKK alpha) | Adapta | −2 | 7 | 3 |
| 100 | Km app | PI4KB (PI4K beta) | Adapta | −3 | 12 | 4 |
| 100 | Km app | PIK3CA/PIK3R1 (p110 alpha/p85 alpha) | Adapta | 16 | 24 | 20 |
| 100 | Km app | PIK3CD/PIK3R1 (p110 delta/p85 alpha) | Adapta | 13 | 21 | 17 |
| 100 | Km app | PIK3CG (p110 gamma) | Adapta | 6 | −1 | 2 |
| 100 | Km app | ABL1 | ZLYTE | 17 | 12 | 14 |
| 100 | Km app | AKT1 (PKB alpha) | ZLYTE | −6 | −9 | −8 |
| 100 | Km app | AKT2 (PKB beta) | ZLYTE | 0 | −9 | −4 |
| 100 | Km app | AKT3 (PKB gamma) | ZLYTE | 3 | 1 | 2 |
| 100 | Km app | AMPK A1/B1/G1 | ZLYTE | 8 | 7 | 7 |
| 100 | Km app | AMPK A2/B1/G1 | ZLYTE | 10 | 11 | 10 |
| 100 | Km app | AURKA (Aurora A) | ZLYTE | 37 | 38 | 38 |
| 100 | 100 | BRAF | ZLYTE | 16 | 17 | 17 |
| 100 | Km app | BTK | ZLYTE | −4 | −2 | −3 |
| 100 | Km app | CAMK2A (CaMKII alpha) | ZLYTE | −1 | 2 | 0 |
| 100 | Km app | CDC42 BPA (MRCKA) | ZLYTE | −1 | −6 | −3 |
| 100 | Km app | CDK1/cyclin B | ZLYTE | 10 | 3 | 6 |
| 100 | Km app | CDK2/cyclin A | ZLYTE | −1 | 8 | 4 |
| 100 | Km app | CDK5/p25 | ZLYTE | −7 | −10 | −8 |
| 100 | Km app | CDK5/p35 | ZLYTE | −2 | 6 | 2 |
| 100 | Km app | CHEK1 (CHK1) | ZLYTE | 10 | 2 | 6 |
| 100 | Km app | CHEK2 (CHK2) | ZLYTE | 1 | 8 | 4 |
| 100 | Km app | CLK1 | ZLYTE | 4 | −7 | −2 |

IB35 kinases profiling at 100 nM

| Compound IB35 Conc (nM) | ATP | Kinase | Technology | % Inhibition 1 | % Inhibition 2 | % Inhibition Avg |
|---|---|---|---|---|---|---|
| 100 | Km app | CSNK1A1 (CK1 alpha 1) | ZLYTE | −3 | −2 | −2 |
| 100 | Km app | CSNK1G1 (CK1 gamma 1) | ZLYTE | 3 | 2 | 3 |
| 100 | Km app | CSNK2A2 (CK2 alpha 2) | ZLYTE | 4 | 3 | 3 |
| 100 | Km app | FRAP1 (mTOR) | ZLYTE | −10 | −18 | −14 |
| 100 | Km app | GRK5 | ZLYTE | −7 | 0 | −4 |
| 100 | Km app | GSK3A (GSK3 alpha) | ZLYTE | 43 | 43 | 43 |
| 100 | Km app | GSK3B (GSK3 beta) | ZLYTE | 23 | 25 | 24 |
| 100 | Km app | IRAK4 | ZLYTE | 3 | −14 | −6 |
| 100 | Km app | ITK | ZLYTE | 17 | 12 | 14 |
| 100 | Km app | JAK1 | ZLYTE | −10 | −6 | −8 |
| 100 | Km app | LCK | ZLYTE | 10 | 8 | 9 |
| 100 | 100 | MAP2K1 (MEK1) | ZLYTE | −20 | −6 | −13 |
| 100 | 100 | MAP2K2 (MEK2) | ZLYTE | 13 | 6 | 9 |
| 100 | Km app | MAPK1 (ERK2) | ZLYTE | 5 | 6 | 6 |
| 100 | Km app | MAPK14 (p38 alpha) Direct | ZLYTE | 2 | 4 | 3 |
| 100 | Km app | MAPK3 (ERK1) | ZLYTE | −8 | 1 | −3 |
| 100 | 100 | MAPK8 (JNK1) | ZLYTE | 4 | 21 | 12 |
| 100 | 100 | MAPK9 (JNK2) | ZLYTE | 3 | −5 | −1 |
| 100 | Km app | MAPKAPK2 | ZLYTE | −2 | 2 | 0 |
| 100 | Km app | MARK1 (MARK) | ZLYTE | 20 | 13 | 17 |
| 100 | Km app | PAK6 | ZLYTE | 1 | −9 | −4 |
| 100 | Km app | PRKACA (PKA) | ZLYTE | −5 | −5 | −5 |
| 100 | Km app | PRKCA (PKC alpha) | ZLYTE | −2 | 2 | 0 |
| 100 | Km app | PRKCB1 (PKC beta I) | ZLYTE | −10 | −10 | −10 |
| 100 | Km app | PRKCD (PKC delta) | ZLYTE | −2 | −12 | −7 |
| 100 | Km app | PRKCE (PKC epsilon) | ZLYTE | 4 | 3 | 3 |
| 100 | Km app | PRKCZ (PKC zeta) | ZLYTE | −3 | −2 | −3 |
| 100 | 100 | RAF1 (cRAF) Y340D Y341D | ZLYTE | 10 | 11 | 10 |
| 100 | Km app | ROCK1 | ZLYTE | −9 | −6 | −7 |
| 100 | Km app | ROCK2 | ZLYTE | 3 | 1 | 2 |
| 100 | Km app | RPS6KA1 (RSK1) | ZLYTE | −3 | 7 | 2 |
| 100 | Km app | RPS6KB1 (p70S6K) | ZLYTE | −3 | −10 | −6 |
| 100 | Km app | SRC | ZLYTE | 8 | 6 | 7 |

As it is evident from the data reported, there was no activity on 58 kinases involved in the Akt pathway, with the only exception for Aurora A and GSK3 which resulted to be inhibited with percentage values of 38%, 43% at 100 nM of the tested compound.

In order to study more in depth the biological properties of the new compounds and to correlate the PDK1 inhibition activity to the in vitro antiproliferative properties, the compounds IB35, SA23 and SA16 were further investigated in a series of biological in vitro assays on U87MG cell lines and stem cells isolated from U87MG cells.

GBM Cell-Line Culture and GSC Isolation.

The U87MG cell line was obtained from the National Institute for Cancer Research of Genoa (Italy) and cultured in DMEM 10% FBS and 2 mM glutamine. To isolate GSCs, approximately $2.0 \times 10^6$ cells were suspended in 1 mL of a defined serum-free Neural Stem Cell (NSC) medium (Daniele, S., et al., Modulation of A1 and A2B adenosine receptor activity: a new strategy to sensitise glioblastoma stem cells to chemotherapy. Cell death & disease, 2014. 5(11): p. e1539). After 3-4 days of culture, the neurospheres were collected, suspended in NSC medium, dissociated into single cells, and plated for the assays. For the long-term treatment of cells, NSC or complete medium containing drugs was replaced every two to three days.

Cell Proliferation Assays of GBM Cells and GSCs.

The human U87MG cells or GSCs were seeded at a density of $3 \times 10^3$ cells/well. After 24 h, the cells were treated from one to seven days with fresh growth medium containing different concentrations of SA16, SA23 or IB35. Following the treatment period, cell proliferation was determined using the MTS assay according to manufacturer's instruction. The absorbance of formazan at 490 nM was measured in a colorimetric assay with an automated plate reader (Victor Wallac 2, Perkin Elmer). The results were calculated by subtracting the mean background from the values obtained from each evaluation and were expressed as the percentage of the control (untreated cells). Sigmoid dose-response curve was generated, from which the $IC_{50}$ values were derived.

Annexin V and 7-AAD Staining in U87MG Cells and in GSCs.

Dual staining with Annexin V coniugated to fluorescein-isothiocyanate (FITC) and 7-amino-actinomysin (7-AAD) was performed using the commercially available kit (Muse Annexin V and Dead Cell Kit; Merck KGaA, Darmstadt, Germany). U87MG cells or GSCs were treated with DMSO (control), SA16, SA23 or IB35 for 72 h or seven days, respectively. At the end of the treatment periods, the percentages of living, apoptotic and dead cells were acquired and analysed by Muse™ Cell Analyzer as previously described (Daniele, S., et al., Combined inhibition of AKT/mTOR and MDM2 enhances Glioblastoma Multiforme cell apoptosis and differentiation of cancer stem cells. Sci. Rep., 2015. 5.).

PDK1 Activity in U87MG Cells and in GSCs.

U87MG cells were cultured in 96-well microplates (5.000 cells/well), and treated for different times with 10 μM SA16, SA23 or IB35. At the end of the treatment period, the GSCs were centrifuged at 500×g for 3 minutes; cells were washed twice using fresh saline, and rapidly fixed with 4% (for adherent U87MG cells) or 8% (for suspension GSCs) formaldehyde to preserve activation of specific protein modification. The activity of PDK1 was assessed measuring the levels of phosphorylated AKT on Thr308, using a specific primary antibodies. The subsequent incubation with a secondary HRP-conjugated antibody and the developing solution allowed the colorimetric quantification of the levels of phosphorylated protein. The relative number of cells in each well was then determined using the Crystal-Violet assay. The results were calculated by subtracting the mean background value from the values obtained under each test condition: values were normalised to the number of cells in each well and were expressed as the percentages of the control (untreated cells) values.

Wound Healing Migration Assay

U87MG cells were plated ($1 \times 10^5$) onto six-well plates up to form a confluent monolayer, and treated for 72 h with 10 µM SA16, SA23 or IB35. The cell monolayer was then scratched in a straight line to make a 'scratch wound' with a 0.2-ml pipette tip and the cell debris was removed by washing the cells with phosphate-buffered saline. RPMI medium supplemented with 1% FBS was added, and images of the closure of the scratch were captured at 0, 6, and 24 h.

Statistical Analysis.

The non-linear multipurpose curve-fitting program Graph-Pad Prism (Graph Pad Software Inc., San Diego, Calif.) was used for data analysis and graphic presentations. All data are presented as the mean±SEM. Statistical analysis was performed by one-way analysis of variance (ANOVA) with Bonferroni's corrected t-test for post-hoc pair-wise comparisons. P<0.05 was considered statistically significant.

Results

Effects of the PDK1 Inhibitors on U87MG Cell Proliferation

As representative GBM cell line, the above U87MG cells were used; this human cell line resulted an appropriate model to study the effects of PDK1 inhibition, because it is deficient for the tumour suppressor phosphatase and tensin homologue (PTEN), a negative regulator of the PI3K/AKT pathway (Wang, S. I., et al., *Somatic mutations of PTEN in glioblastoma multiforme*. Cancer research, 1997. 57(19): p. 4183-4186). To examine the effects of SA16, SA23 and IB35 on GBM cell growth/survival, U87MG cells were incubated with different concentrations of the new compounds (1 nM-10 µM) for 24 and 72 h. Specifically, U87MG cells were treated in complete medium with different concentrations of SA16, SA23 or IB35 (1 nM-10 µM) for 24 h (A) or 72 h (B). At the end of treatment, cell proliferation was measured using the MTS assay. The data are expressed as a percentage with respect to that of untreated cells (control), which was set to 100%, and are the mean values±SEM of three independent experiments, each performed in duplicate. The significance of the differences reported in FIGS. 1 and 2 was determined with a one-way ANOVA with Bonferroni post-test (* p<0.05, p<0.01, * p<0.001 vs. control cells).

Figure 2:
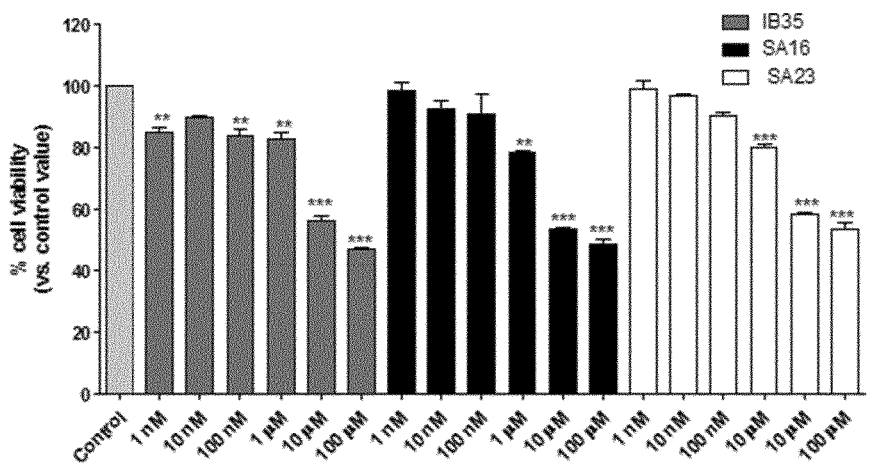
FIG. 2 illustrates the inhibition of U87MG cell proliferation after 72 h of incubation with compounds of the invention.

After 24 h (FIG. 1), the three compounds induced only a modest inhibition of U87MG cell proliferation; the higher effect was observed with IB35 (41% of inhibition, FIG. 1). In contrast, after 72 h all compounds significantly decreased U87MG cell proliferation, in a concentration-dependent manner, yielding $IC_{50}$ values of 449.7±46.2 nM (IB35), 2.05±0.19 µM (SA16) and 1.17±0.10 µM (SA23) (FIG. 2). The ranking of $IC_{50}$ values of the new compounds on U87MG cells reflected the affinity ranking towards recombinant PDK1, thus confirming that the anti-proliferative activities are mediated by PDK1 inhibition.

Effect of PDK1 Inhibitors on the Induction of U87MG Apoptosis

It was then investigated whether the reduction in cell proliferation elicited by the PDK1 inhibitors could be associated with apoptosis. U87MG cells were treated for 72 h with DMSO (control), or 10 µM SA16, SA23 or IB35. At the end of the treatment period, the cells were collected, and the level of phosphatidylserine externalisation was evaluated using the Annexin V-staining protocol, as described above (FIG. 3). In FIG. 4 the data are expressed as the percentage of apoptotic cells (the data for the early-stage apoptotic cells shown in white, and the data for the late-stage apoptotic/necrotic cells shown in grey) versus the total number of cells. The data shown represented the mean±SEM of three different experiments. The significance of the differences was determined with a one-way ANOVA with Bonferroni post-test (*** p<0.001 vs. control).

Figure 3:
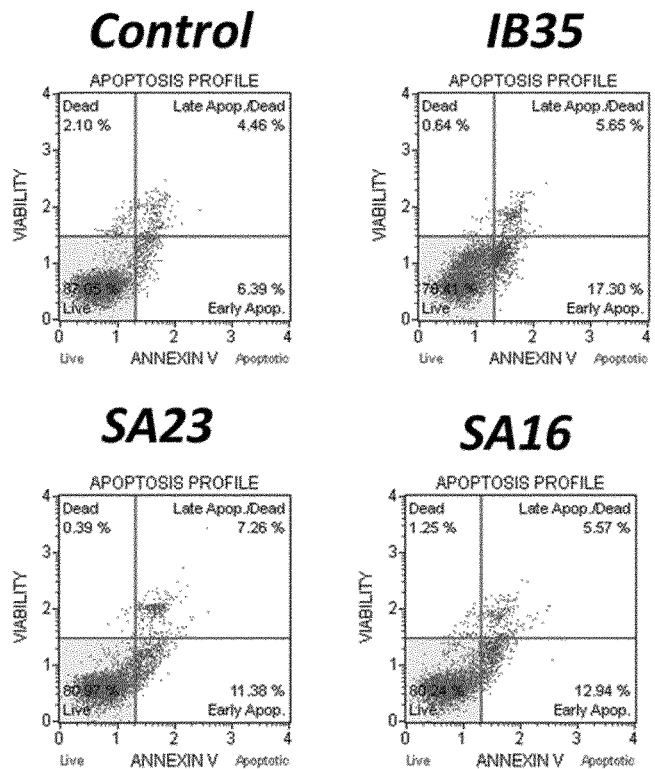
FIG. 3 shows the effects of PDK1 inhibitors of the invention on the induction of U87MG apoptosis using Annexin V-staining protocol.
Figure 4:
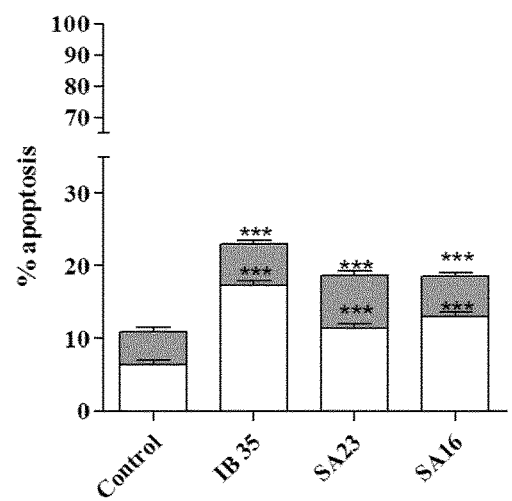
FIG. 4 shows the effects of PDK1 inhibitors of the invention on the induction of U87MG apoptosis as percentage of apoptotic cells versus the total number of cells.

Treatment of U87MG cells with SA16, SA23 and IB35 (10 µM) for 72 h induced a significant phosphatidylserine externalization, both in the absence (early apoptosis), or in the presence of 7-amino-actinomysin binding to DNA (late apoptosis/death) (FIGS. 3 and 4). Consistent with the data obtained in the MTS assay, IB35 showed the highest degree of GBM apoptosis (percentage of total apoptotic cells: 23.0±1.9).

Effects of SA16, SA23 and IB35 on PDK1 Activity in U87 MG Cells

Figure 5:
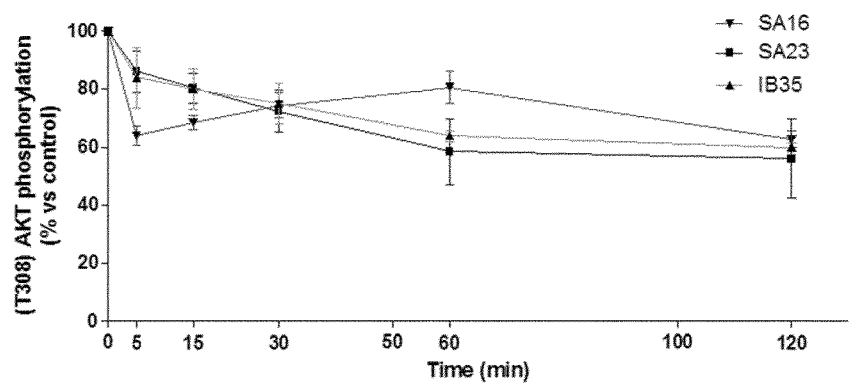
FIG. 5 shows the effects of the compounds of the invention on PDK1 activity in U87 MG cells.

To assess whether SA16, SA23 and IB35 could effectively inhibit the AKT/PDK1 pathway in U87MG cells, U87MG were treated for different times with 10 µM of each inhibitor; following incubation, PDK1 activity was assessed evaluating AKT phosphorylation at Thr308. As reported in literature, U87MG cells displayed a constitutive high level of phosphorylated AKT at both the T308 and Ser473 regulatory sites, in line with a cell profile of cancer cells deficient for PTEN (Gonzalez-Angulo, A. M., et al., SU2C Phase Ib Study of Paclitaxel and MK-2206 in Advanced Solid Tumors and Metastatic Breast Cancer. Journal of the National Cancer Institute, 2015. 107(3): p. dju493; Zinda, M. J., C. J. Vlahos, and M. T. Lai, Ceramide induces the dephosphorylation and inhibition of constitutively activated Akt in PTEN negative U87 mg cells. Biochemical and biophysical research communications, 2001. 280(4): p. 1107-1115). U87MG were hence treated for the indicated times (0-120 min) with complete medium containing DMSO (control), or 10 µM SA16, SA23 or IB35. At the end of the treatment periods, the levels of (T308)AKT phosphorylation was evaluated using an ELISA kit, as described above. The data reported in FIG. 5 were expressed as the percentage of phosphorylated (T308)AKT relative to those of untreated cells (control), which were set at 100%, and were the mean values±SEM of three independent experiments performed in triplicate. As depicted in FIG. 5, SA23 and IB35, tested at 10 µM, significantly inhibited AKT phosphorylation at Thr308, in a time-dependent manner, with a peak of inhibition after 120 min, confirming the compounds were able to block PDK1 activity. In contrast, SA16 elicited a biphasic kinetic of (T308)AKT inhibition, showing peaks after 5 min and 120 min of treatment (FIG. 5).

Effects of PDK1 Inhibitors on the Cell Migration

Figure 6:
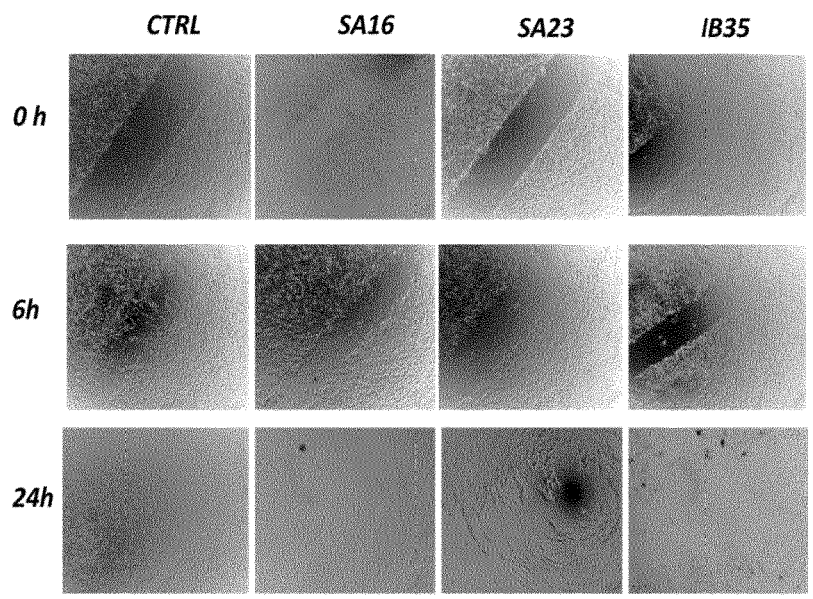
FIG. 6 shows micrographs in the evaluation of effects of the PDK1 inhibitors of the invention on wound healing migration.
Figure 7:
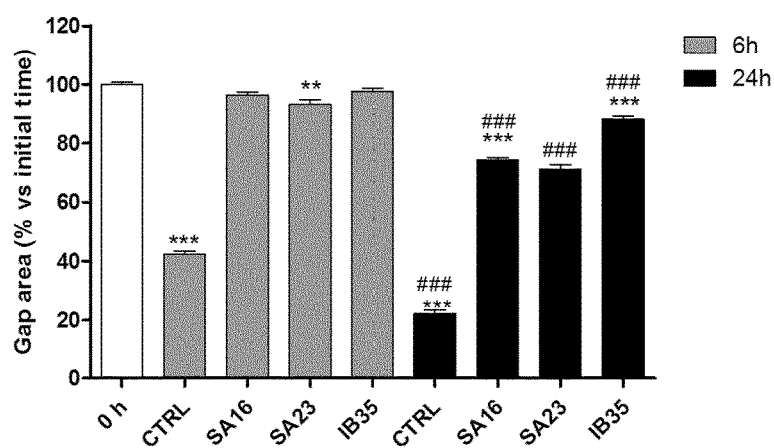
FIG. 7 shows gap area measurements in the evaluation of effects of the PDK1 inhibitors of the invention on wound healing migration.

To assess whether the inhibition of PDK1 activity could be associated to a cell migration block, a scratch wound assay was performed. Representative microscopic images are shown in FIG. 6. U87MG cells were treated for 72 h with DMSO (control), or 10 µM SA16, SA23 and IB35. Then the cell monolayer was scratched (time zero), and cells were allowed to growth in fresh medium. Representative micrographs were taken after 6 h and 24 h from the scratch (FIG. 6). The gap area (FIG. 7) was measured after 6 h and 24 h from the scratch; the counts were the mean values±SEM of three independent experiments. The significance of the differences was determined using a one-way ANOVA with the Bonferroni post-test (P<0.05, *P<0.001 vs control; ###P<0.001 vs respective gap area at 6 h from the scatch).

Quantitative analysis of gap area (FIG. 7) demonstrated that the treatment of U87MG cells with PDK1 inhibitors significantly inhibit cell migration, both after 6 h and 24 h from the scratch. These results confirmed that a PDK1 inhibition leads to a suppression of tumour cell migration.

Effects of SA16, SA23 and IB35 Treatment on GSC Proliferation

The inhibition of PDK1 has been reported as potentially effective therapeutic approach to reduce self-renewal and propagation of GSCs (Signore, M., et al., Combined PDK1 and CHK1 inhibition is required to kill glioblastoma stem-like cells in vitro and in vivo. Cell death & disease, 2014. 5(5): p. e1223). On this basis, the effects of SA16, SA23 and IB35 on GSCs, isolated from U87MG cells as previously reported, were evaluated (Daniele, S., et al., *Modulation of A1 and A28 adenosine receptor activity: a new strategy to sensitise glioblastoma stem cells to chemotherapy*. Cell death & disease, 2014. 5(11): p. e1539). U87MG-derived GSCs were incubated with the indicated concentrations of IB35, SA23 or SA16 for four days (FIG. 8) or seven days (FIG. 9). At the end of the treatment periods, cell proliferation was measured using the MTS assay. The data were expressed as a percentage with respect to that of untreated cells (control), which was set to 100%, and are the mean values±SEM of three independent experiments, each performed in duplicate. $IC_{50}$ values after seven days of treatment were calculated from sigmoid dose-response curve (FIG. 9). The significance of the differences was determined with a one-way ANOVA with Bonferroni post-test ( p<0.01, * p<0.001 vs control).

Figure 8:
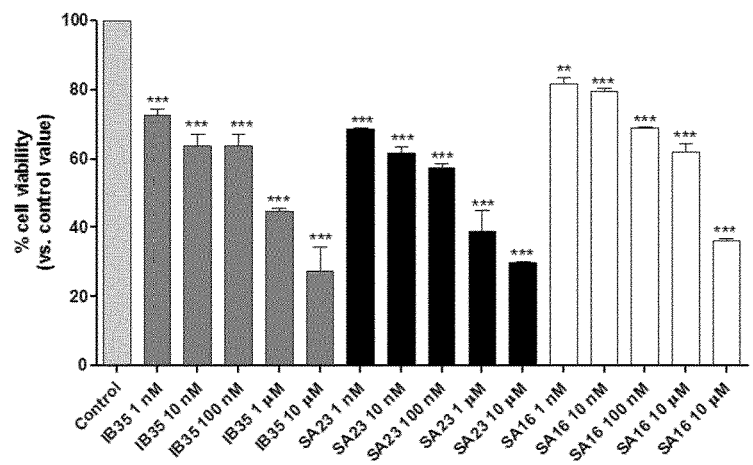
FIG. 8 shows the effects of the treatment of the compounds of the invention on GSC proliferation after four days.
Figure 9:
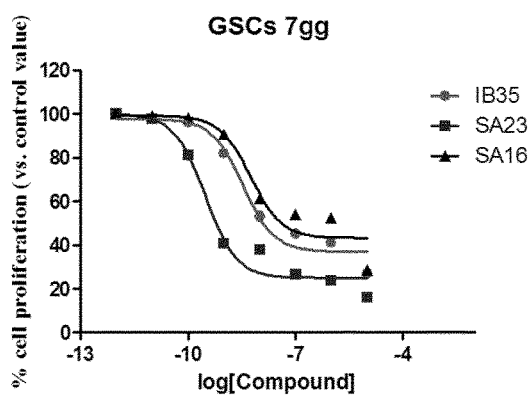
FIG. 9 shows the effects of the treatment of the compounds of the invention on GSC proliferation after seven days.

When GSCs were incubated with IB35 and SA23, a significant inhibition of cell proliferation occurred, starting from four days of treatment (FIG. 8). After seven days of treatment, the compounds induced a concentration-dependent inhibition of GSC proliferation, yielding $IC_{50}$ values of 3.36±0.40 nM (IB35), 0.30±0.04 nM (SA23) and 5.47±0.10 nM (SA16) (FIG. 9). These data confirmed that the PDK1 inhibitors are able to block GSC proliferation.

Effects of PDK1 Inhibitors on GSC Apoptosis

Figure 10:
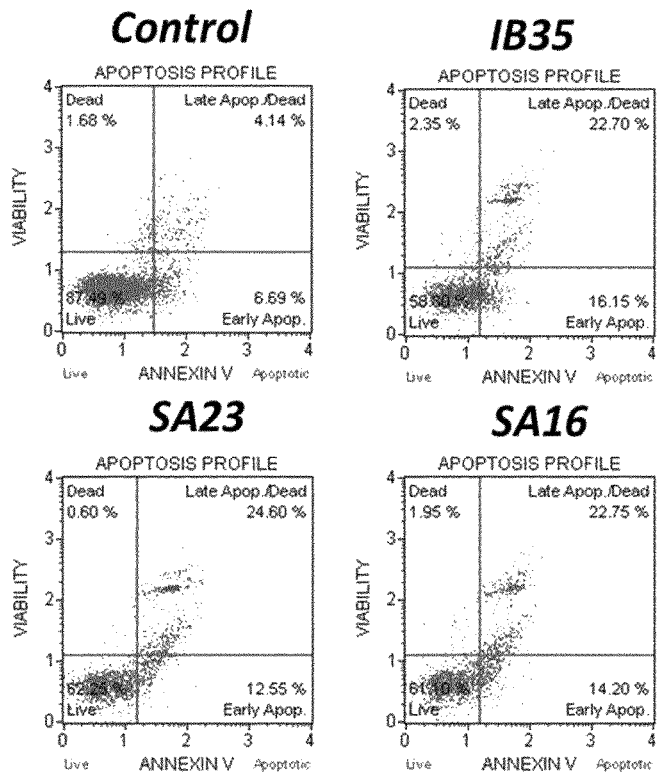
FIG. 10 shows the effects of PDK1 inhibitors of the invention on GSC apoptosis using Annexin V-staining protocol.

It was investigated if the reduction of cell proliferation elicited by the two compounds could be associated to cell apoptosis. GSCs were treated for 7 days with NSC medium containing DMSO (control), or 10 μM of IB35, SA16 or SA23 for seven days. At the end of treatments, the cells were collected and the degree of phosphatidylserine externalisation was evaluated using the Annexin V protocol, as above described (FIG. 10). The data were expressed as the percentage of apoptotic cells (early-apoptotic in white, late-apoptotic/necrotic in grey) relative to the total number of cells and represented in FIG. 11. The data were the mean values±SEM of three different experiments. The significance of the differences was determined with a one-way ANOVA with Bonferroni post-test (*** p<0.001 vs. control).

Figure 11:
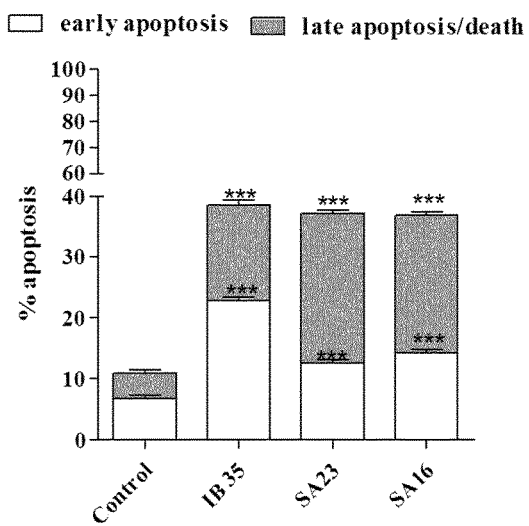
FIG. 11 shows the effects of PDK1 inhibitors of the invention on GSC apoptosis as percentage of apoptotic cells versus the total number of cells.

When Annexin V staining was measured after 7 days of GSC treatment, all compounds induced a significant phosphatidylserine externalization, both in the absence (early apoptosis), or in the presence of 7-amino-actinomysin 11 binding to DNA (late apoptosis/death) (FIGS. 10 and 11). As in U87MG cells, IB35 showed the highest degree of GBM apoptosis (percentage of total apoptotic cells: 38.5±3.9).

Effects of SA16, SA23 and IB35 PDK1 Activity in GSCs

Figure 12:
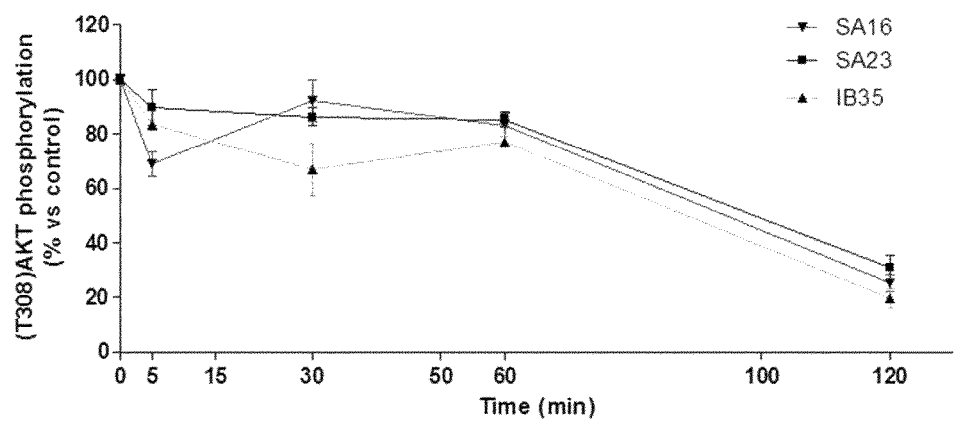
FIG. 12 shows the effects of PDK1 inhibitors of the invention on GSC by ELISA assays.

The effects of the new compounds on PDK1 activity were investigated by ELISA assays also in GSCs. U87MG-derived CSCs were treated for the indicated times (0-120 min) with NSC medium containing DMSO (control), or 10 μM IIB35, SA23 or SA16. At the end of the treatment periods, the levels of AKT phosphorylation on Thr308 were evaluated using an ELISA assay, as above described. The data were expressed as the percentage of phosphorylated AKT relative to those of untreated cells (control), which were set at 100%, and were the mean values±SEM of three independent experiments performed in triplicate. The data are represented in FIG. 12. The significance of differences was performed using one-way ANOVA with Bonferroni post-test (* p<0.05,  p<0.01, * p<0.001 vs. control). Consistent with the data obtained in U87MG cells, SA23 and IB35, tested at 10 μM, significantly inhibited AKT phosphorylation at Thr308, in a time-dependent manner, with a peak of inhibition after 120 min (FIG. 12). In contrast, as evidenced in U87MG cells, SA16 elicited a biphasic kinetic of AKT inhibition, showing peaks after 5 min and 120 min of treatment. Of note, the percentages of PDK1 inhibition were significantly higher in GSCs with respect to U87MG cells (peak of inhibition for IB35: 54.0±5.2 in U87MG cells; 80.4±3.7 in GSCs; peak of inhibition for SA16: 33.3±4.5 in U87MG cells; 74.8±3.0 in GSCs; peak of inhibition for SA23: 48.1±5.0 in U87MG cells; 69.0±4.5 in GSCs.

Comparison of Antiproliferative Activities with a Known Drug in GBM and GSCs

The compounds of the invention IB35, SA16 and SA23 were compared with Everolimus (dihydroxy-12-[(2R)-1-[(1S,3R,4R)-4-(2-hydroxyethoxy)-3-methoxycyclohexyl] propan-2-yl]-19,30-dimethoxy-15,17,21,23,29,35-hexamethyl-11,36-dioxa-4-azatricyclo[30.3.1.0 hexatriaconta-16, 24,26,28-tetraene-2,3,10,14,20-pentone) a gold standard drug of Novartis for targeted-therapy (now in phase I of clinical trials for GBM) (Daniele, S., et al., *Combined inhibition of AKT/mTOR and MDM2 enhances Glioblastoma Multiforme cell apoptosis and differentiation of cancer stem cells*. Sci. Rep., 2015. 5).

The results are reported in the table below.

| Compound | IC50 (nM) PDK1 direct | IC50 U87MG (nM) | IC50 (nM) GSC |
|---|---|---|---|
| IB35 | 112 | 449.7 ± 46.2 | 3.36 ± 0.40 |
| SA16 | 416 | 2050 ± 190 | 5.47 ± 0.10 |
| SA23 | 1520 | 1170 ± 100 | 0.30 ± 0.04 |
| Everolimus (Novartis) | — | 50.0 ± 2.8 | 15.0 ± 1.2 |

The data in table show that even if the IB35 SA16 and SA23 prove to inhibit cell growth on U87 cell line, the potency is lower than Everolimus. On the contrary, the antiproliferative activity against GSC is from 2- to 50-fold higher than Everolimus, indicating that IB35, SA16 and SA23 are more capable in accelerating the induction of apoptosis and thus enhance the inhibition of GSC viability with respect to Everolimus.

From the experimental biological part reported above, the compounds JJ31, IB32, IB35, SA16 and SA23 show to inhibit the PDK1 enzyme with IC50 values in the range of nM to μM.

The ranking of IC50 value on recombinant PDK1 reflected the affinity ranking towards U87MG cell lines, thus confirming that the antiproliferative activity was mediated by PDK1. IB35, SA16 and SA23 inhibited PDK1 constitutive activity in U87MG cells; as a result, the new compounds decreased cell viability, and triggered apoptosis. Moreover, the inhibition of cell viability was long-lasting (72 h). In the wound scratch assay, PDK1 inhibitors showed to significantly inhibit cell migration, both after 6 h and 24 h from the scratch. These results confirmed that a PDK1 inhibition leads to a suppression of tumour cell migration.

Finally, the new compounds were characterized in glioma stem cells (GSCs) isolated from U87MG cells. The results obtained indicated that new compounds induced a time- and concentration-dependent inhibition of GSC proliferation and triggered apoptosis, thus confirming that PDK1 inhibitors were able to block GSC proliferation.

The invention claimed is:

1. A method for the treatment of pathologies requiring an inhibitor of PDK1 enzyme, wherein the method comprises the step of administering to a patient in need thereof a 2-oxo-1,2-dihydropyridine-3-carboxamide compound of Formula (I)

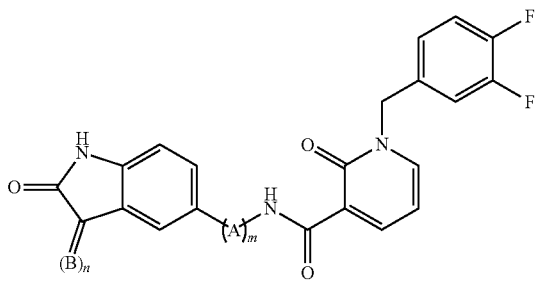

wherein
m is 0 or 1
n is 0 or 1
A is selected from the group consisting of (—NH—CO—CH$_2$—), (—NH—CO—CH(Ph)-), (—NH—CO—CH$_2$—CH$_2$—), (—NH—CO—CH$_2$—CH$_2$—CH$_2$—) and (—NH—CO-Ph-); and
B is CH-D, where D is selected from the group consisting of thienyl, phenyl, and imidazolyl, D is optionally substituted with a halogen,
or a pharmaceutical salt thereof.

2. The method of claim 1, wherein m is 0 and n is 1.
3. The method of claim 1, wherein m is 1 and n is 1.
4. The method of claim 1, wherein A is (—NH—CO—CH$_2$—), (—NH—CO—CH$_2$—CH$_2$—CH$_2$—), (—NH—CO—CH$_2$—CH$_2$), or (—NH—CO-Ph).
5. The method of claim 4, wherein A is (—NH—CO—CH$_2$—) or (—NH—CO—CH$_2$—CH$_2$).
6. The method of claim 1, wherein n is 1 and B is CH-D, where D is imidazolyl.
7. The method of claim 1, wherein said compound is selected from the group consisting of (Z)—N-(3-((1H-imidazol-5-yl)methylene)-2-oxoindolin-5-yl)-1-(3,4-difluorobenzyl)-2-oxo-1,2-dihydropyridine-3-carboxamide, 1-(3,4-difluorobenzyl)-2-oxo-N-(2-oxo-2-((2-oxoindolin-5-yl)amino)ethyl)-1,2-dihydropyridine-3-carboxamide, (E/Z)-1-(3,4-difluorobenzyl)-2-oxo-N-(2-oxo-2-((2-oxo-3-(thiophen-2-ylmethylene)indolin-5-yl)amino)ethyl)-1,2-dihydropyridine-3-carboxamide, (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—(R)—N-(2-((3-(1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide, (E/Z)-1-(3,4-difluorobenzyl)-2-oxo-N-(3-oxo-3-((2-oxo-3-(thiophen-2-ylmethylene)indolin-5-yl)amino)propyl)-1,2-dihydropyridine-3-carboxamide, (Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide, (E/Z)-1-(3,4-difluorobenzyl)-N-(3-((3-(4-fluorobenzylidene)-2-oxoindolin-5-yl)amino)-3-oxopropyl)-2-oxo-1,2-dihydropyridine-3-carboxamide, (Z/E)-N-(3-((3-((1H-imidazol-2-yl)methylene)-2-oxoindolin-5-yl)amino)-3-oxopropyl)-1-(3,4-difluorobenzyl)-2-oxo-1,2-dihydropyridine-3-carboxamide, (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, (E/Z)-1-(3,4-difluorobenzyl)-2-oxo-N-(3-((2-oxo-3-(thiophen-2-ylmethylene)indolin-5-yl)carbamoyl)phenyl)-1,2-dihydropyridine-3-carboxamide, (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide and (E/Z)-1-(3,4-difluorobenzyl)-2-oxo-N-(4-oxo-4-((2-oxo-3-(thiophen-2-ylmethylene)indolin-5-yl)amino)butyl)-1,2-dihydropyridine-3-carboxamide.

8. The method of claim 7, wherein said compound is selected from the group (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—(R)—N-(2-((3-41H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, and (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide.

9. The method of claim 8, wherein the compound of is (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide.

10. The method of claim 1, wherein the pathology that requires a PDK1 inhibitor is a cancer.

11. A 2-oxo-1,2-dihydropyridine-3-carboxamide compound of Formula (II)

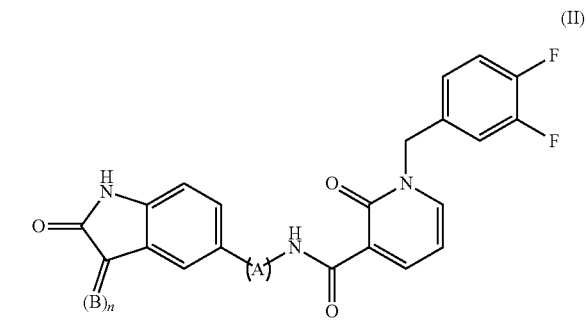

wherein n is 0 or 1

B is CH-D, where D is selected from the group consisting of thienyl, phenyl, and imidazolyl, D is optionally substituted with a halogen; and A is selected from the group consisting of (—NH—CO—CH₂—), (—NH—CO—CH(Ph)-), (—NH—CO—CH₂—CH₂—), (—NH—CO—CH₂—CH₂—CH₂—) and (—NH—CO-Ph-)

or a pharmaceutical salt thereof.

12. The compound of claim 11, wherein A is selected from the group consisting of (—NH—CO—CH₂—), (—NH—CO—CH₂—CH₂—), (—NH—CO—CH₂—CH₂—CH₂—) and (—NH—CO-Ph-).

13. The compound of claim 12, wherein A is (—NH—CO—CH₂—).

14. The compound of claim 11, wherein n is 1 and B is CH-D, where D is imidazolyl.

15. The compound of claim 11, wherein said compound is selected from the group consisting of (E/Z)-1-(3,4-difluorobenzyl)-2-oxo-N-(2-oxo-2-((2-oxo-3-(thiophe-2-ylmethylene)indolin-5-yl)amino)ethyl)-1,2-dihydropyridine-3-carboxamide, (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydro pyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—(R)—N-(2-((3-((1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide, (E/Z)-1-(3,4-difluorobenzyl)-2-oxo-N-(3-oxo-3-((2-oxo-3-(thiophen-2-ylmethylene)indolin-5-yl)amino)propyl)-1,2-dihydropyridine-3-carboxamide, (Z)—N-(3-((3-((1H-imidazol-5-yl)methylene)-2-oxoindolin-5-yl)amino)-3-oxopropyl)-1-(3,4-difluorobenzyl)-2-oxo-1,2-dihydropyridine-3-carboxamide, (E/Z)-1-(3,4-difluorobenzyl)-N-(3-((3-(4-fluorobenzylidene)-2-oxoindolin-5-yl)amino)-3-oxopropyl)-2-oxo-1,2-dihydropyridine-3-carboxamide, (Z/E)-N-(3-((3-((1H-imidazol-2-yl)methylene)-2-oxoindolin-5-yl)amino)-3-oxopropyl)-1-(3,4-difluorobenzyl)-2-oxo-1,2-dihydropyridine-3-carboxamide, (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, (E/Z)-1-(3,4-difluorobenzyl)-2-oxo-N-(3-((2-oxo-3-(thiophen-2-ylmethylene)indolin-5-yl)carbamoyl)phenyl)-1,2-dihydropyridine-3-carboxamide, (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide and (E/Z)-1-(3,4-difluorobenzyl)-2-oxo-N-(4-oxo-4-((2-oxo-3-(thiophen-2-ylmethylene)indolin-5-yl)amino)butyl)-1,2-dihydropyridine-3-carboxamide.

16. The compound of claim 15, wherein said compound is selected from the group (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydropyridine-3-carboxamide, (Z)—(R)—N-(2-((3-((1H-imidazol-5-yl)methylene)-2-oxoindolin-5-yl)amino)-2-oxo-1-phenylethyl)-1-(3,4-difluorobenzyl)-2-oxo-1,2-dihydropyridine-3-carboxamide, and (Z)—(R)—N-(2-((3-((1H-imidazol-2-yl)methylene)-2-oxoindolin-5-yl)amino)-2-oxo-1-phenylethyl)-1-(3,4-difluorobenzyl)-2-oxo-1,2-dihydropyridine-3-carboxamide, (Z)—N-(3-((3-((1H-imidazol-5-yl)methylene)-2-oxoindolin-5-yl)carbamoyl)phenyl)-1-(3,4-difluorobenzyl)-2-oxo-1,2-dihydropyridine-3-carboxamide, and (Z)—N-(4-((3-((1H-imidazol-5-yl)methylene)-2-oxoindolin-5-yl)amino)-4-oxobutyl)-1-(3,4-difluorobenzyl)-2-oxo-1,2-dihydropyridine-3-carboxamide.

17. The compound of claim 14, wherein the compound is (Z)—N-(2-((3-((1H-imidazol-5-yl)methylene)-2-oxoindolin-5-yl)amino)-2-oxoethyl)-1-(3,4-difluorobenzyl)-2-oxo-1,2-dihydro pyridine-3-carboxamide.

18. A pharmaceutical composition comprising the 2-oxo-1,2-dihydropyridine-3-carboxamide compound of claim 11 and a pharmaceutically acceptable carrier.

19. A method for the treatment of pathologies which require an inhibitor of PDK1 enzyme, wherein the method comprises the step of administering to a patient in need thereof, the 2-oxo-1,2-dihydropyridine-3-carboxamide compound of claim 11 or a pharmaceutical salt thereof.

20. The method of claim 19, wherein the pathology is selected from the group consisting of diabetes, neurodegenerative diseases, and cancer.

21. The method of claim 20, wherein the pathology is a cancer.

* * * * *